United States Patent
Ho et al.

(10) Patent No.: US 10,358,472 B2
(45) Date of Patent: Jul. 23, 2019

(54) HIGH AFFINITY CD47 ANALOGS

(71) Applicant: The Board of Trustees of the Leland Stanford Junior University, Stanford, CA (US)

(72) Inventors: Chia Chi Ho, Los Altos Hills, CA (US); Kenan Christopher Garcia, Menlo Park, CA (US); Aaron Michael Ring, New Haven, CT (US); Kipp Andrew Weiskopf, Brookline, MA (US); Irving L. Weissman, Stanford, CA (US); Nan Guo Ring, New Haven, CT (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/569,007

(22) PCT Filed: May 5, 2016

(86) PCT No.: PCT/US2016/030997
§ 371 (c)(1),
(2) Date: Oct. 24, 2017

(87) PCT Pub. No.: WO2016/179399
PCT Pub. Date: Nov. 10, 2016

(65) Prior Publication Data
US 2018/0127480 A1    May 10, 2018

Related U.S. Application Data

(60) Provisional application No. 62/157,874, filed on May 6, 2015.

(51) Int. Cl.
| | | |
|---|---|---|
| *C07K 14/705* | (2006.01) | |
| *C07K 16/30* | (2006.01) | |
| *A61K 38/17* | (2006.01) | |
| *A61K 39/395* | (2006.01) | |
| *G01N 33/50* | (2006.01) | |
| *A61K 38/00* | (2006.01) | |

(52) U.S. Cl.
CPC .... *C07K 14/70503* (2013.01); *A61K 38/1774* (2013.01); *A61K 39/39558* (2013.01); *C07K 14/70596* (2013.01); *C07K 16/30* (2013.01); *G01N 33/5005* (2013.01); *A61K 38/00* (2013.01); *C07K 2319/21* (2013.01); *C07K 2319/24* (2013.01); *C07K 2319/30* (2013.01); *C07K 2319/50* (2013.01)

(58) Field of Classification Search
CPC ........ C07K 14/70503; C07K 14/70596; A61K 38/1774
See application file for complete search history.

(56) References Cited

U.S. PATENT DOCUMENTS

| 7,691,970 B2 * | 4/2010 | Skerra | C07K 14/43504 530/350 |
|---|---|---|---|
| 8,377,448 B2 * | 2/2013 | Smith | C07K 14/70596 424/185.1 |
| 2004/0147731 A1 | 7/2004 | Parkos | |
| 2008/0131431 A1 | 6/2008 | Smith et al. | |
| 2010/0239578 A1 | 9/2010 | Danska et al. | |
| 2010/0239579 A1 | 9/2010 | Smith et al. | |

FOREIGN PATENT DOCUMENTS

| DE | 4417598 A1 | 12/1995 |
|---|---|---|
| WO | 2010/070047 A1 | 6/2010 |
| WO | 2013/109752 A1 | 7/2013 |

OTHER PUBLICATIONS

Chao et al., "Anti-CD47 Antibody Synergizes with Rituximab to Promote Phagocytosis and Eradicate Non-Hodgkin Lymphoma", Cell, Sep. 3, 2010, pp. 699-713, vol. 142, Issue 5, Elsevier Inc., Amsterdam, Netherlands.

Hatherley et al., "Paired receptor specificity explained by structures of signal regulatory proteins alone and complexed with CD47", Mol Cell., Jul. 25, 2008. pp. 266-277, 31(2), Elsevier Inc., Amsterdam, Netherlands.

Hatherley et al., "The structure of the macrophage signal regulatory protein alpha (SIRPalpha) inhibitory receptor reveals a binding face reminiscent of that used by T cell receptors", May 11, 2007, pp. 14567-14575, vol. 282, No. 19, The American Society for Biochemistry and Molecular Biology, Inc., Rockville, MD.

(Continued)

*Primary Examiner* — Bao Q Li
(74) *Attorney, Agent, or Firm* — Pamela J. Sherwood; Bozicevic, Field & Francis LLP

(57) ABSTRACT

High affinity CD47 reagents are provided, which (i) comprise at least one amino acid change relative to the wild-type protein; and (ii) have an increased affinity for a SIRPα relative to the wild-type protein. Compositions and methods are provided for modulating phagocytosis in a mammal by administering a therapeutic dose of a pharmaceutical composition comprising a high affinity CD47 reagent, which blocks the physiological binding interaction between SIRPα and a ligand, e.g., native CD47.

12 Claims, 10 Drawing Sheets
(8 of 10 Drawing Sheet(s) Filed in Color)
Specification includes a Sequence Listing.

(56) References Cited

OTHER PUBLICATIONS

Ho et al., "Velcro engineering of high affinity CD47 ectodomain as signal regulatory protein a (SIRPa) antagonists that enhance antibody-dependent cellular phagocytosis," J Biol Chem., Apr. 2, 2015, pp. 12650-12663, vol. 290, No. 20, The American Society for Biochemistry and Molecular Biology, Inc., Rockville, MD.

Lee et al., "Identification and characterization of a novel human PP1 phosphatase complex", J.B.C., Jun. 1, 2010, pp. 37953-37963, 285, The American Society for Biochemistry and Molecular Biology, Inc., Rockville, MD.

Lee et al., "Novel structural determinants on SIRPα that mediate binding to CD47", J. Immunol., Dec. 1, 2007, pp. 7741-7750, vol. 179, Issue 11, American Association of Immunologists, Inc., Rockville, MD.

Lin et al., "Soluble extracellular domains of human SIRPα and CD47 expressed in *Escherichia coli* enhances the phagocytosis of leukemia cells by macrophages in vitro", Protein Expr Purif., Sep. 2012, pp. 109-116, vol. 85, Issue 1, Elsevier Inc., Amsterdam, Netherlands.

Rebres et al. "Normal Ligand Binding and Signaling by CD47 (Integrin-associated Protein) Requires a Long Range Disulfide Bond between the Extracellular and Membrane-spanningDomains," The Journal of Biological Chemistry, Jul. 13, 2001, pp. 34607-34616, vol. 276, No. 37, The American Society for Biochemistry and Molecular Biology, Inc., Rockville, MD.

Research Watch, "High-Affinity SIRPα Variants Potentiate Antibody Therapy Efficacy", Cancer Discov. Jun. 6, 2013, p. 716, vol. 3, Issue 7, American Association for Cancer Research, Philadelphia, PA.

Weiskopf et al. "Engineered SIRPα Variants as Immunotherapeutic Adjuvants to Anticancer Antibodies", Science, Jul. 5, 2013, pp. 88-91, vol. 341, Issue 6141, American Association for the Advancement of Science, Washington, D.C.

Weiskopf et al., "Improving macrophage responses to therapeutic antibodies by molecular engineering of SIRPα variants", Oncoimmunology, Sep. 1, 2013, pp. e25773-1 to e25773-3, vol. 2 Issue 9, Landes Bioscience, Austin, TX.

* cited by examiner

| | -3 | -2 | -1 | 1 | 3 | 53 | 54 |
|---|---|---|---|---|---|---|---|
| WT | | | | Q | L | A | L |
| N361 | W | Q | R | P | R | W | A |
| N362 | W | A | P | P | R | Y | T |
| N363 | W | Q | P | L | D | D | K |
| N364 | W | Q | P | L | A | | M |
| N365 | W | A | P | L | R | | |
| N366 | W | Q | T | P | K | | |
| N368 | W | Q | F | P | R | | |
| N369 | W | Q | I | P | N | | |
| N3610 | W | Q | P | L | L | E | W |
| N3612 | W | Q | P | L | | Q | A |
| N3614 | W | Q | P | L | K | | A |
| N3617 | W | Q | R | P | R | | |
| N3618 | W | Q | L | P | | E | I |
| N3621 | W | Q | I | P | E | | |
| N3622 | W | G | P | L | R | | |
| N3623 | W | Q | M | P | V | V | T |
| N3624 | W | Q | I | P | R | Q | V |
| Consensus | W | Q | | P | P | | |

FIG. 4A

N363 C15G full amino acid sequence (SEQ ID NO: 5):

WQLPLLFNKTKSVEFTFGNDTVVIPCFVTNMEAQNTTEVYVKWKFKGRDIYTFDGDKNKSTVPTDFSSAKIEVSQLLKGDASLKMDKSDAVSHTGNYT
CEVTELTREGETIIELKYRVVS

N3612 C15G full amino acid sequence (SEQ ID NO: 6):

WQPPLLFNKTKSVEFTFGNDTVVIPCFVTNMEAQNTTEVYVKWKFKGRDIYTFDGQANKSTVPTDFSSAKIEVSQLLKGDASLKMDKSDAVSHTGNY
TCEVTELTREGETIIELKYRVVS

N3612 C15 full amino acid sequence (SEQ ID NO: 7):

WQPPLLFNKTKSVEFTFCNDTVVIPCFVTNMEAQNTTEVYVKWKFKGRDIYTFDGQANKSTVPTDFSSAKIEVSQLLKGDASLKMDKSDAVSHTGNYT
CEVTELTREGETIIELKYRVVS

N3612 F14C full amino acid sequence (SEQ ID NO: 8):

WQPPLLFNKTKSVEFTCGNDTVVIPCFVTNMEAQNTTEVYVKWKFKGRDIYTFDGQANKSTVPTDFSSAKIEVSQLLKGDASLKMDKSDAVSHTGNY
TCEVTELTREGETIIELKYRVVS

FIG. 4D

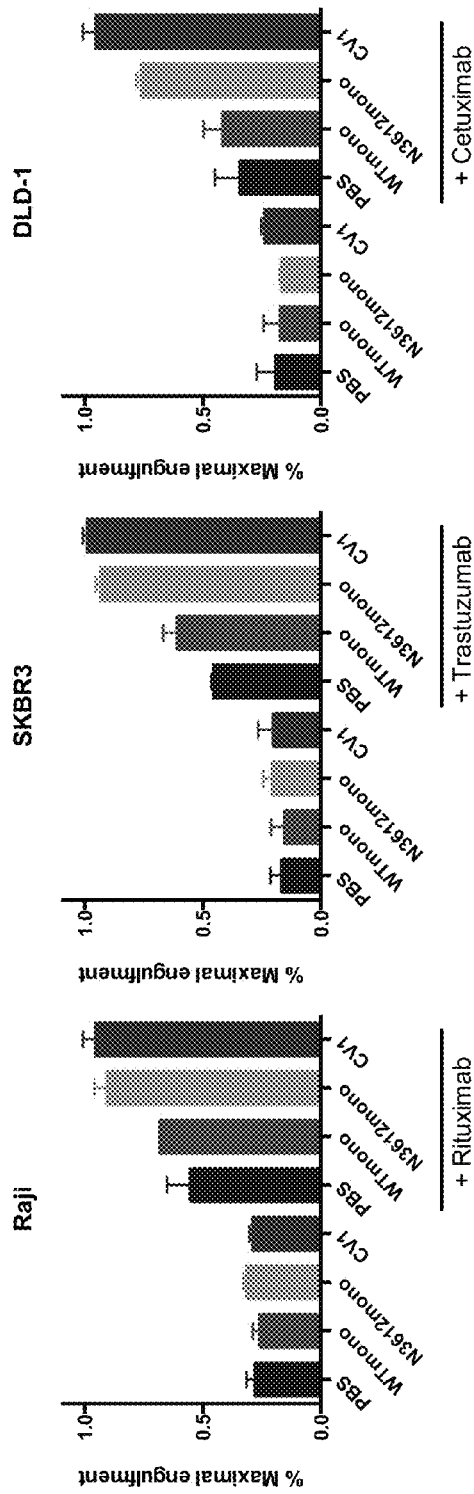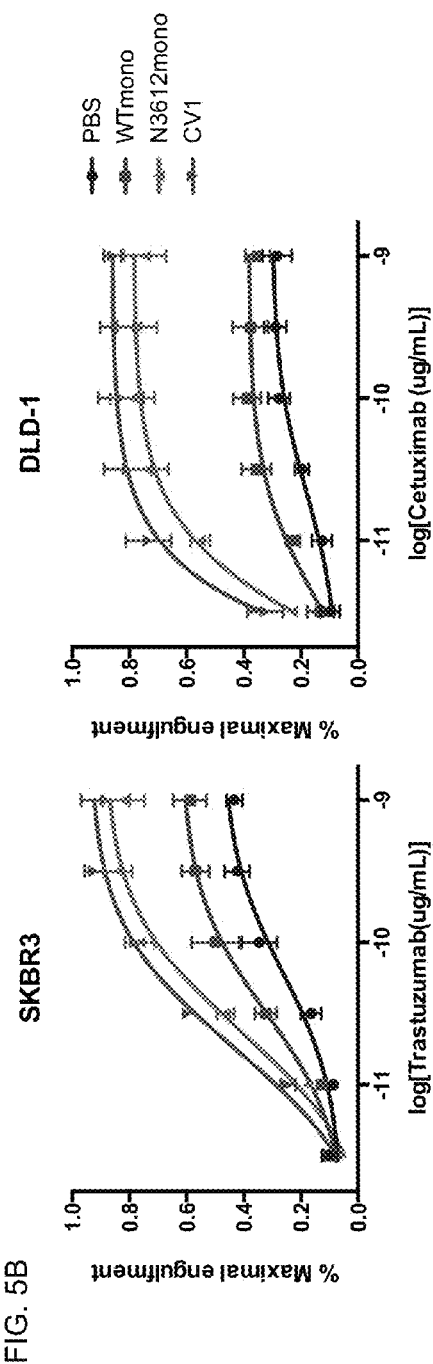
FIG. 5A
FIG. 5B

SEQUENCE LISTING

<160> NUMBER OF SEQ ID NOS: 9

<210> SEQ ID NO 1
<211> LENGTH: 293
<212> TYPE: PRT
<213> ORGANISM: Homo sapiens

<400> SEQUENCE: 1

```
Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
```

```
                210                 215                 220
Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
                260                 265                 270

Ser Gly Leu Ser Ile Leu Ala Leu Ala Gln Leu Leu Gly Leu Val Tyr
                275                 280                 285

Met Lys Phe Val Glu
        290

<210> SEQ ID NO 2
<211> LENGTH: 275
<212> TYPE: PRT
<213> ORGANISM: Homo sapiens

<400> SEQUENCE: 2

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
                20                  25                  30

Thr Thr Glu Val Tyr Val Lys Trp Lys Phe Lys Gly Arg Asp Ile Tyr
                35                  40                  45

Thr Phe Asp Gly Ala Leu Asn Lys Ser Thr Val Pro Thr Asp Phe Ser
            50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
                100                 105                 110

Tyr Arg Val Val Ser Trp Phe Ser Pro Asn Glu Asn Ile Leu Ile Val
                115                 120                 125

Ile Phe Pro Ile Phe Ala Ile Leu Leu Phe Trp Gly Gln Phe Gly Ile
            130                 135                 140

Lys Thr Leu Lys Tyr Arg Ser Gly Gly Met Asp Glu Lys Thr Ile Ala
145                 150                 155                 160

Leu Leu Val Ala Gly Leu Val Ile Thr Val Ile Val Ile Val Gly Ala
                165                 170                 175

Ile Leu Phe Val Pro Gly Glu Tyr Ser Leu Lys Asn Ala Thr Gly Leu
                180                 185                 190

Gly Leu Ile Val Thr Ser Thr Gly Ile Leu Ile Leu Leu His Tyr Tyr
                195                 200                 205

Val Phe Ser Thr Ala Ile Gly Leu Thr Ser Phe Val Ile Ala Ile Leu
                210                 215                 220

Val Ile Gln Val Ile Ala Tyr Ile Leu Ala Val Val Gly Leu Ser Leu
225                 230                 235                 240

Cys Ile Ala Ala Cys Ile Pro Met His Gly Pro Leu Leu Ile Ser Gly
                245                 250                 255

Leu Ser Ile Leu Ala Leu Ala Gln Leu Leu Gly Leu Val Tyr Met Lys
                260                 265                 270

Phe Val Glu
        275
```

<210> SEQ ID NO 3
<211> LENGTH: 125
<212> TYPE: PRT
<213> ORGANISM: Homo sapiens

<400> SEQUENCE: 3

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn Ile
        115                 120                 125

<210> SEQ ID NO 4
<211> LENGTH: 117
<212> TYPE: PRT
<213> ORGANISM: Homo sapiens

<400> SEQUENCE: 4

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser
        115

<210> SEQ ID NO 5
<211> LENGTH: 120
<212> TYPE: PRT
<213> ORGANISM: Homo sapiens

<400> SEQUENCE: 5

Trp Gln Leu Pro Leu Leu Phe Asn Lys Thr Lys Ser Val Glu Phe Thr
1               5                   10                  15

Phe Gly Asn Asp Thr Val Val Ile Pro Cys Phe Val Thr Asn Met Glu
            20                  25                  30

Ala Gln Asn Thr Thr Glu Val Tyr Val Lys Trp Lys Phe Lys Gly Arg

```
            35                  40                  45
Asp Ile Tyr Thr Phe Asp Gly Asp Lys Asn Lys Ser Thr Val Pro Thr
     50                  55                  60

Asp Phe Ser Ser Ala Lys Ile Glu Val Ser Gln Leu Leu Lys Gly Asp
 65                  70                  75                  80

Ala Ser Leu Lys Met Asp Lys Ser Asp Ala Val Ser His Thr Gly Asn
                 85                  90                  95

Tyr Thr Cys Glu Val Thr Glu Leu Thr Arg Glu Gly Thr Ile Ile
                100                 105                 110

Glu Leu Lys Tyr Arg Val Val Ser
            115                 120
```

<210> SEQ ID NO 6
<211> LENGTH: 120
<212> TYPE: PRT
<213> ORGANISM: Homo sapiens

<400> SEQUENCE: 6

```
Trp Gln Pro Pro Leu Leu Phe Asn Lys Thr Lys Ser Val Glu Phe Thr
 1               5                  10                  15

Phe Gly Asn Asp Thr Val Val Ile Pro Cys Phe Val Thr Asn Met Glu
                20                  25                  30

Ala Gln Asn Thr Thr Glu Val Tyr Val Lys Trp Lys Phe Lys Gly Arg
            35                  40                  45

Asp Ile Tyr Thr Phe Asp Gly Gln Ala Asn Lys Ser Thr Val Pro Thr
     50                  55                  60

Asp Phe Ser Ser Ala Lys Ile Glu Val Ser Gln Leu Leu Lys Gly Asp
 65                  70                  75                  80

Ala Ser Leu Lys Met Asp Lys Ser Asp Ala Val Ser His Thr Gly Asn
                 85                  90                  95

Tyr Thr Cys Glu Val Thr Glu Leu Thr Arg Glu Gly Glu Thr Ile Ile
                100                 105                 110

Glu Leu Lys Tyr Arg Val Val Ser
            115                 120
```

<210> SEQ ID NO 7
<211> LENGTH: 120
<212> TYPE: PRT
<213> ORGANISM: Homo sapiens

<400> SEQUENCE: 7

```
Trp Gln Pro Pro Leu Leu Phe Asn Lys Thr Lys Ser Val Glu Phe Thr
 1               5                  10                  15

Phe Cys Asn Asp Thr Val Val Ile Pro Cys Phe Val Thr Asn Met Glu
                20                  25                  30

Ala Gln Asn Thr Thr Glu Val Tyr Val Lys Trp Lys Phe Lys Gly Arg
            35                  40                  45

Asp Ile Tyr Thr Phe Asp Gly Gln Ala Asn Lys Ser Thr Val Pro Thr
     50                  55                  60

Asp Phe Ser Ser Ala Lys Ile Glu Val Ser Gln Leu Leu Lys Gly Asp
 65                  70                  75                  80

Ala Ser Leu Lys Met Asp Lys Ser Asp Ala Val Ser His Thr Gly Asn
                 85                  90                  95

Tyr Thr Cys Glu Val Thr Glu Leu Thr Arg Glu Gly Glu Thr Ile Ile
                100                 105                 110

Glu Leu Lys Tyr Arg Val Val Ser
```

```
<210> SEQ ID NO 8
<211> LENGTH: 120
<212> TYPE: PRT
<213> ORGANISM: Homo sapiens

<400> SEQUENCE: 8

Trp Gln Pro Pro Leu Leu Phe Asn Lys Thr Lys Ser Val Glu Phe Thr
1               5                   10                  15

Cys Gly Asn Asp Thr Val Val Ile Pro Cys Phe Val Thr Asn Met Glu
                20                  25                  30

Ala Gln Asn Thr Thr Glu Val Tyr Val Lys Trp Lys Phe Lys Gly Arg
            35                  40                  45

Asp Ile Tyr Thr Phe Asp Gly Gln Ala Asn Lys Ser Thr Val Pro Thr
        50                  55                  60

Asp Phe Ser Ser Ala Lys Ile Glu Val Ser Gln Leu Leu Lys Gly Asp
65                  70                  75                  80

Ala Ser Leu Lys Met Asp Lys Ser Asp Ala Val Ser His Thr Gly Asn
                85                  90                  95

Tyr Thr Cys Glu Val Thr Glu Leu Thr Arg Glu Gly Glu Thr Ile Ile
            100                 105                 110

Glu Leu Lys Tyr Arg Val Val Ser
        115                 120

<210> SEQ ID NO 9
<211> LENGTH: 15
<212> TYPE: PRT
<213> ORGANISM: Artificial Sequence
<220> FEATURE:
<223> OTHER INFORMATION: Biotin acceptor tag

<400> SEQUENCE: 9

Gly Leu Asn Asp Ile Phe Glu Ala Gln Lys Ile Glu Trp His Glu
1               5                   10                  15
```

HIGH AFFINITY CD47 ANALOGS

CROSS-REFERENCE

This application is a 371 application and claims the benefit of PCT Application No. PCT/US2016/030997, filed May 5, 2016, which claims benefit of U.S. Provisional Patent Application Ser. No. 62/157,874, filed May 6, 2015, which applications are incorporated herein by reference in their entirety.

FEDERALLY SPONSORED RESEARCH AND DEVELOPMENT

This invention was made with Government support under contracts CA086065 and CA177684 awarded by the National Institutes of Health. The Government has certain rights in the invention.

BACKGROUND OF THE INVENTION

Turnover of cells begins with the induction of an apoptotic program or other cellular changes that mark them for removal, and the subsequent recognition of markers by phagocytes, including macrophages, dendritic cells, and the like. This process requires a specific and selective removal of unwanted cells. Discrimination of the healthy from the unwanted/aged/dying cells display markers or ligands called "eat-me" signals, i.e. "altered self", which can in turn be recognized by receptors on the phagocytes. Healthy cells may display "don't eat-me" signals that actively inhibit phagocytosis; these signals are either downregulated in the dying cells or present in an altered conformation. The cell surface protein CD47 on healthy cells and its engagement of a phagocyte receptor, SIRPα, constitutes a key "don't eat-me" signal that can turn off engulfment mediated by multiple modalities, including apoptotic cell clearance and FcR mediated phagocytosis. Blocking the CD47 mediated engagement of SIRPα on a phagocyte, or the loss of CD47 expression in knockout mice, can cause removal of live cells and non-aged erythrocytes. Alternatively, blocking SIRPα recognition also allows engulfment of targets that are not normally phagocytosed.

CD47 is a broadly expressed transmembrane glycoprotein with a single Ig-like extracellular domain and five membrane spanning regions. CD47 functions as a cellular ligand for SIRPα with binding mediated through the $NH_2$-terminal V-like domain of SIRPα. SIRPα is expressed primarily on myeloid cells, including macrophages, granulocytes, myeloid dendritic cells (DCs), mast cells, and their precursors, including monocytes and hematopoietic stem cells. Structural determinants on SIRPα that mediate CD47 binding are discussed by Lee et al. (2007) J. Immunol. 179: 7741-7750; Hatherley et al. (2007) J.B.C. 282:14567-75; and the role of SIRPα cis dimerization in CD47 binding is discussed by Lee et al. (2010) J.B.C. 285:37953-63.

In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo. CD47 is also constitutively upregulated on a number of cancers. Overexpression of CD47 by tumor cells may increase pathogenicity by allowing the cell to evade phagocytosis.

SUMMARY OF THE INVENTION

High-affinity CD47 polypeptides and analogs thereof are provided, sometimes referred to herein as high-affinity CD47 reagents. The reagents are modified forms of the native human CD47 protein, e.g., having additional and/or variant amino aid residues, and have utility for in vivo and in vitro methods that block the interaction between native SIRPα and CD47.

The interaction between CD47 and SIRPα ligands is increasingly recognized as a key regulator of macrophages that can be targeted to elicit macrophage-mediated anti-tumor response. Existing modulators of this pathway generally target the ubiquitously expressed CD47 cell surface molecule (see, e.g., Chao et al. Cell 2010 Sep. 3; 142(5): 699-713; Weiskopf et al. Science. 2013 Jul. 5; 341(6141): 88-91). However, because of CD47's ubiquitous expression, there is a large antigen sink for such CD47-targeted agents (e.g., monomeric or dimeric high-affinity SIRPα variants) as well as a high potential for off-target effects. To address these and other issues, the present disclosure provides an alternative strategy to antagonize (or block) the interaction between native CD47 and native SIRPα. Specifically, the present disclosure provides high-affinity CD47 molecules that target SIRPα rather than CD47.

As described below, a library of CD47 binding domain variants was generated and screened for members having high affinity for multiple human SIRPα alleles. The library of CD47 binding domain variants included CD47 molecules having N-termini that were extended by three random amino acid residues, which were predicted to make more contact with SIRPα. In addition, the library of CD47 binding domain variants included amino acid changes or insertions in the loop region (amino acids 53 and 54 of the mature CD47 polypeptide).

Multiple high-affinity CD47 reagents were identified in this screen and were characterized. As shown below, high-affinity CD47 reagents improved the phagocytosis of target cells ex vivo and could be conjugated to detectable labels for use as staining reagents to identify cells expressing SIRPα. Thus, high-affinity CD47 reagents find use in numerous applications, including but not limited to cancer immunotherapy (e.g., as adjuvants to tumor-specific antibodies); as imaging reagents (e.g., for detecting and tracking macrophages, for autoimmune and inflammatory disease states, etc).

In one embodiment, the invention provides soluble high affinity CD47 reagents, which lack the CD47 transmembrane domain, and comprise at least one amino acid change relative to wild-type human CD47, which amino acid change increases the affinity of the CD47 polypeptide binding to SIRPα. The high affinity CD47 polypeptide may be post-translationally modified, for example by glycosylation, pegylation, etc. In some embodiments, the high affinity CD47 reagent is a fusion protein comprising an Fc domain. In certain embodiments, the high affinity CD47 reagent includes a cysteine substitution or the addition of a cysteine residue that enables coupling chemistry, e.g., efficient conjugation of the high affinity CD47 reagent to a detection agent, a therapeutic agent (e.g., a drug), a multimerizing agent, or other functional group.

The invention also includes pharmaceutical formulations of high affinity CD47 reagents in combination with a pharmaceutically acceptable excipient. Such formulations may be provided as a unit dose, e.g. a dose effective to increase targeted phagocytosis in an individual. Pharmaceutical formulations also include lyophilized or other preparations of the high affinity CD47 reagents, which may be reconstituted for use.

In some embodiments, methods are provided to manipulate targeted phagocytosis of cells, e.g. by macrophages or other mammalian phagocytic cells. In such methods, a cell expressing SIRPα is contacted with a high affinity CD47 reagent of the invention in a dose effective to block the interaction between endogenous CD47 and SIRPα. Blocking this interaction allows engulfment of targets that are not normally phagocytosed. The contacting may be performed in vivo, e.g. for therapeutic purposes, and in vitro, e.g. for screening assays and the like. The high affinity CD47 reagent for these purposes may be multimeric; or monomeric. Monomeric reagents find particular use for administration in combination with an antibody that selectively binds to the cell targeted for phagocytosis.

In related embodiments, tumor cells, e.g. solid tumors such as carcinomas, sarcomas, melanomas, etc.; leukemias; lymphomas, etc. are targeted for phagocytosis by contacting the phagocytic cells in proximity of the tumor cells with a dose of a high affinity CD47 polypeptide that is effective to block, or mask SIRPα on the surface of the phagocytic cell, allowing engulfment of targets that are not normally phagocytosed. Administration of an effective dose of high affinity CD47 polypeptide to a patient prevents interaction between CD47 and SIRPα, which increases the clearance of tumor cells via phagocytosis. For these purposes it can be advantageous to administer a high affinity CD47 variant in the presence of an immunoglobulin Fc bound to the cell targeted for phagocytosis, which provides a pro-phagocytic signal. In these aspects, the high affinity CD47 polypeptide can be combined with monoclonal antibodies directed against one or more additional tumor cell markers, which compositions can be synergistic in enhancing phagocytosis and elimination of tumor cells as compared to the use of single agents. Monomeric high affinity CD47 reagents are advantageous for this purpose as they have low red blood cell toxicity. Alternatively a high affinity CD47 fusion construct comprising an immunoglobulin Fc region, e.g. one that provides a pro-phagocytic signal, may be administered.

In other embodiments the high affinity CD47 reagent comprises a detectable label, e.g., conjugated to a cysteine residue. Such a labeled reagent can be used for imaging purposes in vitro or in vivo, e.g. in the imaging of phagocytes.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 3A Schematic of strategy to increase CD47 affinity for SIRPα by N-terminal and loop extension. FIG. 3B Extension library design. Residues colored in pale orange (Q1, L3, G52, A53 and L54 sites in the mature form of CD47) are native to CD47 and were included in the randomization. Residues colored in dark blue indicate the 3 additional amino acids that were added for N-terminal extension (labeled −1, −2, and −3), and residues colored in cyan (designated 53_x, where x is 1, 2, 3, or 4) represent the 0, 2, or 4 additional amino acids that were added for loop extension between A53 and L54. All three types of molecules were mixed and selected as a single extension library. FIG. 3C Histogram overlays assessing SIRPα a1d1 (Left) and a2d1 (Right) staining of the library at each round of selection (described in detail in the Examples section).

FIGS. 4A, 4B, 4C and 4D. Sequence analysis and biophysical characterizations of high affinity CD47 variants. FIG. 4A Summary of sequences of engineered CD47 variants. The position of mutated residues and their corresponding sequence in wild-type is denoted at the top of the table (an empty space in the non-WT variants indicates that a WT amino acid is present at that site; there are no residues present at −1, −2 and −3 positions in the WT sequence). Red text color indicates the consensus mutations and are listed at the bottom. FIG. 4B Surface plasmon resonance (SPR) sensorgram of WT CD47 (Left) and a representative high affinity CD47 variant N363 (Right) binding to human SIRPα allele 1 domain 1 (a1d1). FIG. 4C Surface plasmon resonance (SPR) sensorgram for binding to human SIRPα allele 2 domain 1 (a2d1). FIG. 4D Sequences of representative high-affinity CD47 (SEQ ID NOs: 5 to 8).

FIGS. 5A and 5B. Ex vivo functional characterization of high affinity CD47 variants: high affinity CD47 monomer is an adjuvant to monoclonal antibodies to increase phagocytosis of cancer cells. FIG. 5A Primary human macrophage phagocytosis of GFP+Raji lymphoma (Left), GFP+SKBR3 breast cancer (Middle) and GFP+DLD-1 colon cancer (Right) cells treated with PBS (Blue), WT CD47 monomer (Red), high affinity N3612 C15G (SEQ ID NO:5; Orange) or Super-SIRPα CV1 (Purple) (described in Weiskopf et al. (2013) Engineered SIRPα variants as immunotherapeutic adjuvants to anticancer antibodies. Science 341, 88-91; hereby incorporated by reference herein in its entirety) with or without respective tumor-specific monoclonal antibodies [rituximab (Rituxan®, Genentech; left panel); trastuzumab (Herceptin®, Genentech; middle panel); or cetuximab (Erbitux®, Bristoll-Myers Squibb; right panel)]. Proteins were used at 1 uM, and the antibodies were used at 10 ug/ml. FIG. 5B Dose-response of macrophage phagocytosis of GFP+ SKBR3 breast cancer (Left) and GFP+DLD-1 colon cancer (Right) cells treated with titrating amounts of tumor-specific monoclonal antibodies [trastuzumab (Herceptin®, Genentech; left panel); or cetuximab (Erbitux®, Bristoll-Myers Squibb; right panel)] in the presence of 1 uM of the protein treatments listed [WT CD47 monomer (WTmono), N3612 C15G monomer (N3612mono), Super-SIRPα CV1 (CV1)] as compared to control PBS treatment.

FIG. 6A Schematic of the Cysteine installed for maleimide linking chemistry: either the WT Cysteine at position 15 is restored (the "C15" variant; the CD47 used in library construction had a C15G mutation) or the phenylalanine at position 14 is replaced with Cysteine (F14C). FIG. 6B Graph showing binding of different CD47 species to SIRPα a1d1-expressing yeast in titration experiments. Shown are: biotinylated WT CD47 (Blue), biotinylated high affinity CD47 variant N3612 C15G (Red; SEQ ID NO:6), N3612 F140 coupled to Alexa Fluor 647 (Green; SEQ ID NO:8), and N3612 C15 coupled to Alexa Fluor 647 (Purple; SEQ ID NO:7). FIG. 6C Graph showing binding to SIRPα a2d1-expressing yeast in titration experiments (CD47 species are the same as in FIG. 6B). FIG. 6D Staining of human peripheral blood using FMO control (Blue), high affinity CD47 variant N3612-Alexa 647 (Red; SEQ ID NO:6), and a commercially available anti-SIRPα antibody-Alexa 647 (clone 15-414 eBioscience; Green).

DEFINITIONS

Figure 1:
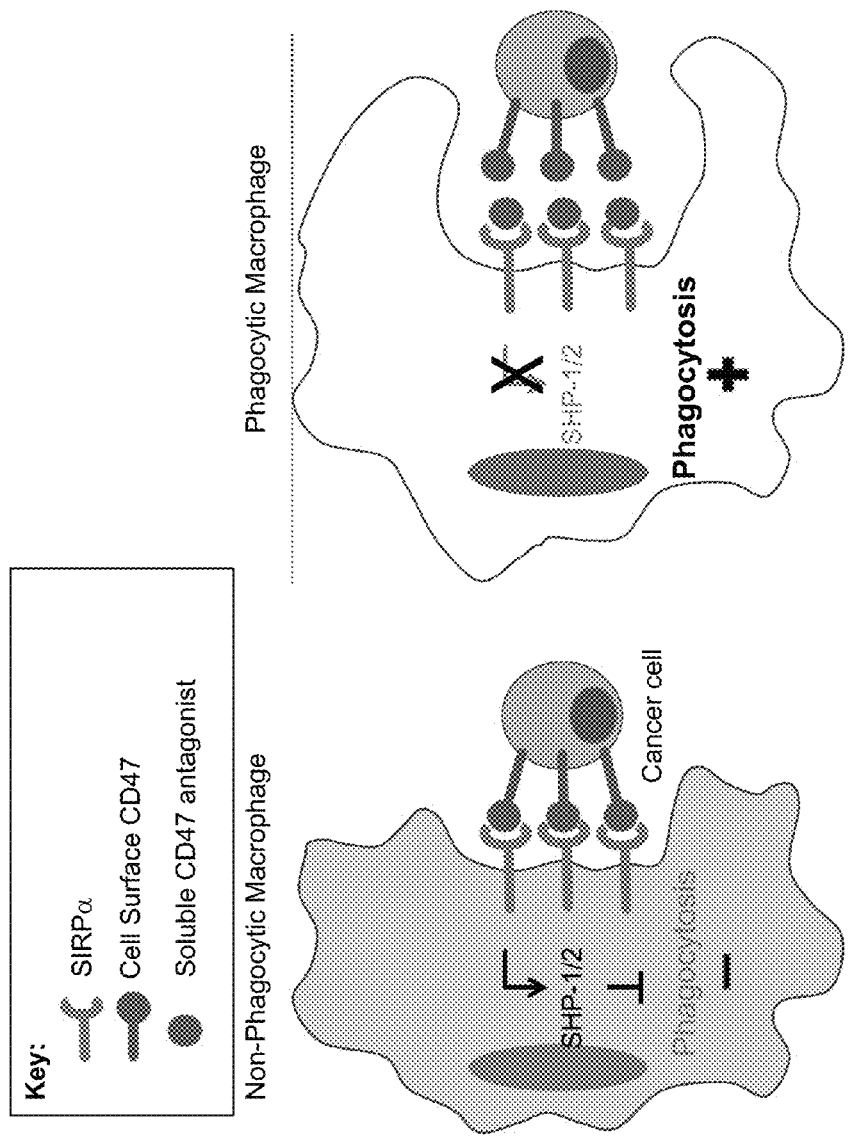
FIG. 1. Schematic of SIRPα blockade by soluble high-affinity CD47. (Left) CD47 expression on cancer cells activates SIRPα on macrophages, recruiting SHP-1 and 2 tyrosine phosphatases and preventing macrophage phagocytosis of cancer cells. (Right) Soluble high-affinity CD47 prevents CD47 on cancer cell surface from engaging SIRPα on macrophages, thereby acting as a competitive antagonist.

In the description that follows, a number of terms conventionally used in the field of cell culture are utilized. In order to provide a clear and consistent understanding of the specification and claims, and the scope to be given to such terms, the following definitions are provided.

The terms "inhibitors," "blocking agents", "antagonizing agents" and "masking agents" (and the like) of the interaction between SIRPα and its ligand CD47 refer to molecules that prevent the binding of SIRPα and CD47, e.g., the high affinity CD47 reagents disclosed. For development purposes the binding may be performed under experimental conditions, e.g. using isolated proteins as binding partners, using portions of proteins as binding partners, using yeast display of proteins or portions of proteins as binding partners, and the like.

For physiologically relevant purposes the binding of SIRPα and CD47 is usually an event between two cells, where each cell expresses one of the binding partners. Of particular interest is the expression of SIRPα on phagocytic cells and their precursors (e.g., macrophages and monocytes); and the expression of CD47 on cells that could be targets for phagocytosis, e.g. tumor cells, circulating hematopoietic cells, and the like. Inhibitors may be identified using in vitro and in vivo assays for receptor or ligand binding or signaling.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer. Subjects may be human, but also include other mammals, particularly those mammals useful as laboratory models for human disease, e.g. mouse, rat, etc.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias. Examples of cancer include but are not limited to, ovarian cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor.

Metastasis can also be defined as several steps of a process, such as the departure of cancer cells from an original tumor site, and migration and/or invasion of cancer cells to other parts of the body.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as ovarian cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the terms "treatment," "treating," and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

Treating may refer to any indicia of success in the treatment or amelioration or prevention of an cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with cancer or other diseases. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

In some embodiments, treatment is accomplished by administering a combination of a high affinity CD47 reagent of the invention with a cytotoxic agent. One exemplary class of cytotoxic agents are chemotherapeutic agents. Exemplary chemotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, duocarmycin, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol™), pilocarpine, prochloroperazine, rituximab, saproin, tamoxifen, taxol, topotecan hydrochloride, trastuzumab, vinblastine, vincristine and vinorelbine tartrate.

In other embodiments, administration of a high affinity CD47 reagent of the invention is combined with an effective dose of an agent that increases patient hematocrit, for example erythropoietin stimulating agents (ESA). Such agents are known and used in the art, including, for example, Aranesp® (darbepoetin alfa), Epogen®NF/Procrit®NF (epoetin alfa), Omontys® (peginesatide), Procrit®, etc.

Other combination therapies include administration with cell-specific antibodies, for example antibodies selective for tumor cell markers, radiation, surgery, and/or hormone deprivation (Kwon et al., Proc. Natl. Acad. Sci U.S.A., 96: 15074-9, 1999). Angiogenesis inhibitors can also be combined with the methods of the invention.

A number of antibodies are currently in clinical use for the treatment of cancer, and others are in varying stages of clinical development. For example, there are a number of antigens and corresponding monoclonal antibodies for the treatment of B cell malignancies. One target antigen is CD20. Rituximab is a chimeric unconjugated monoclonal antibody directed at the CD20 antigen. CD20 has an important functional role in B cell activation, proliferation, and differentiation. The CD52 antigen is targeted by the monoclonal antibody alemtuzumab, which is indicated for treatment of chronic lymphocytic leukemia. CD22 is targeted by a number of antibodies, and has recently demonstrated efficacy combined with toxin in chemotherapy-resistant hairy cell leukemia. Two new monoclonal antibodies targeting CD20, tositumomab and ibritumomab, have been submitted to the Food and Drug Administration (FDA). These antibodies are conjugated with radioisotopes. Alemtuzumab (Campath) is used in the treatment of chronic lymphocytic leukemia; Gemtuzumab (Mylotarg) finds use in the treatment of acute myelogenous leukemia; Ibritumomab (Zevalin) finds use in the treatment of non-Hodgkin's lymphoma; Panitumumab (Vectibix) finds use in the treatment of colon cancer.

Monoclonal antibodies useful in the methods of the invention that have been used in solid tumors include, without limitation, edrecolomab and trastuzumab (herceptin). Edrecolomab targets the 17-1A antigen seen in colon and rectal cancer, and has been approved for use in Europe for these indications. Trastuzumab targets the HER-2/neu antigen. This antigen is seen on 25% to 35% of breast cancers. Cetuximab (Erbitux) is also of interest for use in the methods of the invention. The antibody binds to the EGF receptor (EGFR), and has been used in the treatment of solid tumors including colon cancer and squamous cell carcinoma of the head and neck (SCCHN).

In addition to cancer therapies, the high affinity CD47 reagents of the invention are useful in other therapies in which monoclonal antibodies are administered for the purpose of depleting cells, e.g. in the treatment of inflammatory diseases by depletion immune cells. For such purposes the high affinity CD47 reagent of the invention is administered in combination with a therapeutic antibody, e.g. with rituximab for depletion of B cells in inflammatory diseases and autoimmune conditions; alemtuzumab for multiple sclerosis; OKT3 for immunosuppression; others for bone marrow transplant conditioning; and the like.

"Concomitant administration" of a cancer therapeutic drug, ESA or tumor-directed antibody with a pharmaceutical composition of the present invention means administration with the high affinity CD47 reagent at such time that both the drug, ESA or antibody and the composition of the present invention will have a therapeutic effect. Such concomitant administration may involve concurrent (i.e. at the same time), prior, or subsequent administration of the drug, ESA or antibody with respect to the administration of a compound of the invention. A person of ordinary skill in the art would have no difficulty determining the appropriate timing, sequence and dosages of administration for particular drugs and compositions of the present invention.

As used herein, the phrase "disease-free survival," refers to the lack of such tumor recurrence and/or spread and the fate of a patient after diagnosis, with respect to the effects of the cancer on the life-span of the patient. The phrase "overall survival" refers to the fate of the patient after diagnosis, despite the possibility that the cause of death in a patient is not directly due to the effects of the cancer. The phrases, "likelihood of disease-free survival", "risk of recurrence" and variants thereof, refer to the probability of tumor recurrence or spread in a patient subsequent to diagnosis of cancer, wherein the probability is determined according to the process of the invention.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

DETAILED DESCRIPTION OF THE EMBODIMENTS

Figure 2:
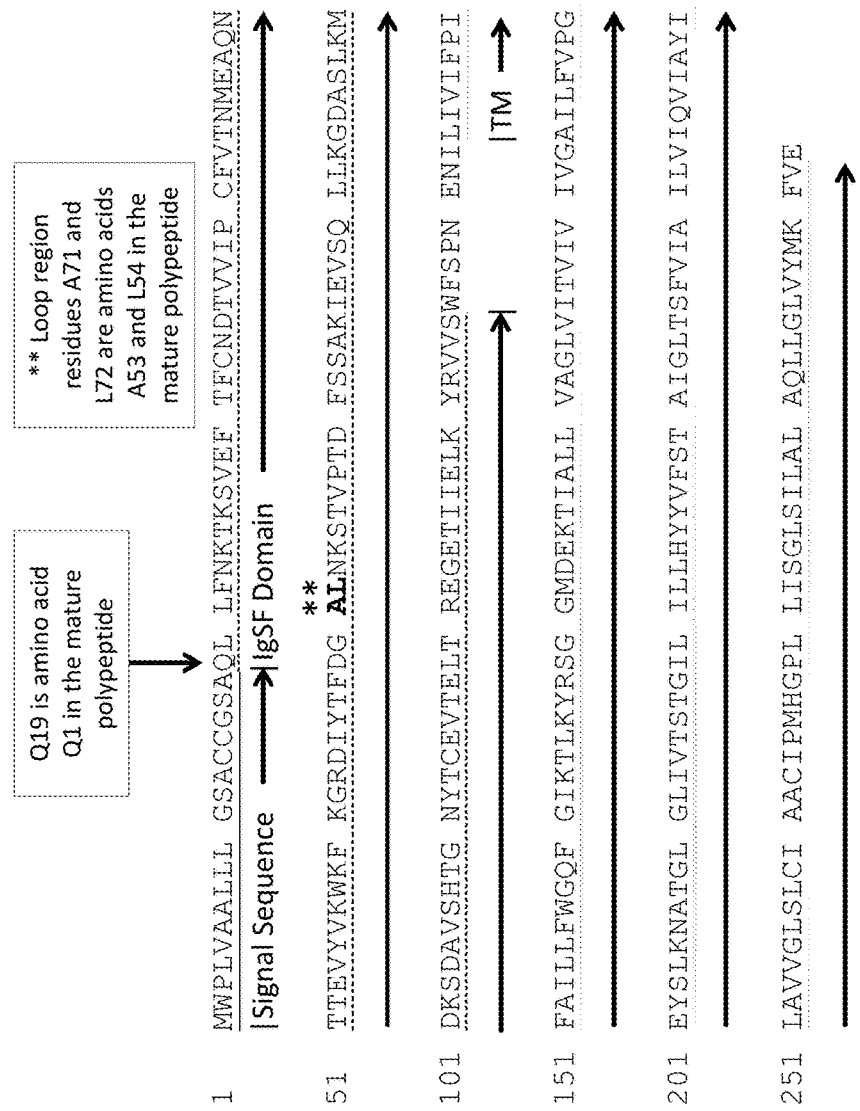
FIG. 2. Amino acid sequence of full length CD47 (SEQ ID NO:1; 293 amino acids). The signal sequence (amino acids 1 to 18, underlined), the soluble IgSF domain (amino acids 19 to 135, dotted underline), and the transmembrane domain (TM; amino acids 144 to 292, underlined) are indicated. The description of the high affinity CD47 variants herein generally refers to amino acid positions based on the mature form of CD47 (i.e., without the signal sequence; e.g., SEQ ID NO:2). Thus, Q19 of the full-length CD47 (i.e., with the signal sequence; SEQ ID NO:1) is Q1 in the mature form (e.g., SEQ ID NO:2) and amino acids A71 and L72 of the full length form (in bold; also called the loop region below) are A53 and L54 in the mature form.

High affinity CD47 polypeptides and analogs thereof are provided, which may be referred to generically as high affinity CD47 reagents. In certain embodiments, the reagents are variants of the native human CD47 protein. In one embodiment, the present invention provides a soluble CD47 variant polypeptide, wherein the polypeptide lacks the CD47 transmembrane domain and comprises at least one amino acid change relative to the wild-type CD47 sequence (see the domain structure of human CD47 shown in FIG. 2), and wherein the amino acid change increases the affinity of the CD47 polypeptide binding to a one or more SIRPα alleles, for example by at least 10-fold, at least 20-fold, at least 50-fold, at least 100-fold, at least 500-fold, at least 1000-fold or more.

Amino acid changes include any naturally occurring or man-made amino acid modifications known or later discovered in the field. In some embodiments, amino acid changes include, e.g., substitution of one or more amino acid, deletion of one or more amino acid, addition of one or more amino acid, insertion of one or more amino acid, or any combination thereof, etc. In some embodiments, amino acid changes include replacing an existing amino acid with another amino acid. In some embodiments, amino acid changes include adding one or more (e.g., 1, 2, 3, 4, 5, 6, 7, 8, 9, 10 or more) amino acids to the N terminus of the mature form of CD47. In related embodiments, amino acid changes include replacing one or more existing amino acids with non-natural amino acids, or inserting or adding one or more non-natural amino acids. Amino acid changes may be made in at least 1, 2, 3, 4, 5, 6, 7, 8, 9, 10, 11, 12 or more amino acid residues relative to a native sequence. The one or more amino acid changes alter properties of CD47, e.g., affecting the stability, binding activity and/or specificity, etc.

In certain embodiments, the high affinity CD47 reagent of the invention comprises at least one amino acid added to the N-terminus of the mature protein (i.e., the protein without the signal sequence). For human CD47, such amino acid additions are present immediately upstream of amino acid Q19 of the full length CD47 sequence (amino acids 1 to 18 are the signal sequence in SEQ ID NO:1 and is indicated in FIG. 2; Q19 of the full length CD47 polypeptide (SEQ ID NO:1) is Q1 of the mature form of CD47 (SEQ ID NO:2). In certain embodiments, the high affinity CD47 reagent includes at least 2 amino acids added to the N-terminus of the mature protein, including at least 3 amino acids, at least 4 amino acids, at least 5 amino acids or more added to the N-terminus of the mature protein.

High affinity CD47 polypeptides can be at least about 100 amino acids in length, at least about 110, at least about 120, at least about 130, amino acids in length. In certain embodiments, the high affinity CD47 polypeptide does not include any of the polypeptide sequence in the transmembrane domain, i.e. after about amino acid L144 of the full length sequence, as shown in FIG. 2. In certain embodiments, the high affinity CD47 polypeptide is a variant of SEQ ID NO:3 (the extracellular domain of CD47) or SEQ ID NO:4 (the IgSF domain of CD47). In certain embodiments, the high affinity CD47 polypeptide is fused to a heterologous polypeptide sequence, e.g. immunoglobulin Fc.

Additional aspects of the disclosure include shorter peptides from the high affinity CD47 reagents, where the shorter peptides bind to SIRPα and include at least one amino acid change set forth herein. Such high affinity CD47-derived peptides usually comprise a contiguous stretch of amino acids from a sequence set forth herein of not more than 10 amino acids in length, not more than 15 amino acids in length, not more than 20, not more than 25, not more than 30 amino acids, not more than 35 amino acids, not more than 40 amino acids, not more than 45 amino acids, not more than 50 amino acids, not more than 55 amino acids, not more than 60 amino acids, not more than 65 amino acids, not more than 70 amino acids, not more than 75 amino acids, not more than 80 amino acids, not more than 85 amino acids, not more than 90 amino acids, not more than 95 amino acids, not more than 100 amino acids.

In some embodiments, amino acid changes in the high affinity CD47 polypeptide are made at the N-terminal domain of CD47. Amino acid changes include, without limitation, the addition of amino acid residues to the N-terminus, i.e., upstream of Q1 in the mature CD47 polypeptide (numbering defined by the mature CD47 sequence of, set forth as SEQ ID NO:2). The number of added amino acids includes 1 or more, 2 or more, 3 or more, 4 or more, 5 or more, etc. In certain embodiments, three amino acids are added to the N-terminus of the mature CD47 polypeptide. In certain embodiments, the three amino acids added have the formula $X_{-3}X_{-2}X_{-1}$ (from N to C), where $X_{-3}$ is W; $X_{-2}$ is selected from Q, A and G; and $\lambda_{-1}$ is selected from R, P, L, T, F, I, and M. In certain embodiments, the three amino acids added are selected from: WQR, WAP, WQL, WQP, WQT, WQF, WQI, WGP, and WQM.

In some embodiments, amino acid changes in the high affinity CD47 polypeptide are substitutions made at one or more of amino acids Q1, L3, A53, and L54 (based on the mature form of CD47; SEQ ID NO:2). In certain embodiments, the high affinity CD47 reagent includes a substitution at Q1 selected from Q1P and Q1L. In certain embodiments, the high affinity CD47 reagent includes a substitution at L3 selected from L3R, L3A, L3K, L3N, L3E, and L3V. In certain embodiments, the high affinity CD47 reagent includes a substitution at A53 selected from A53W, A53Y, A53D, A53Q, and A53V. In certain embodiments, the high affinity CD47 reagent includes a substitution at L54 selected from L54A, L54I, L54K, L54M, L54E, L54W, L54S, L54I, and L54V. In certain embodiments, the high affinity CD47 reagent includes one or more substitutions selected from: (1) Q1P and Q1L; (2) L3R, L3A, L3K, L3N, L3E, and L3V; (3) A53W, A53Y, A53D, A53Q, and A53V; and (4) L54A, L54I, L54K, L54M, L54E, L54W, L54S, L54I, and L54V. In some embodiments the high affinity CD47 polypeptide comprises modifications selected from (1) to (4) above, at two, three, or all four of the residues; and combinations and conservative equivalents thereof.

Sets of amino acid changes may include combinations of N-terminal additions and amino acid substitutions as described above. Thus, in certain embodiments, high affinity CD47 reagents include a three amino acid addition at the N-terminus and one or more substitutions at positions selected from Q1, L3, A53 and L54 as described above. FIG. 4 A provides non-limiting examples of high affinity CD47 reagents having both an N-terminal addition of three amino acids and one or more amino acid substitutions.

High affinity CD47 reagents of the invention comprise the portion of CD47 that is sufficient to bind SIRPα at a recognizable affinity, e.g., high affinity, which normally lies between the signal sequence and the transmembrane domain, or a fragment thereof that retains the binding activity.

High affinity CD47 reagents of the present invention can be further modified, e.g., joined to a wide variety of other oligopeptides or proteins for a variety of purposes. For example, post-translationally modified, for example by prenylation, acetylation, amidation, carboxylation, glycosylation, pegylation, etc. Such modifications can also include modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. In some embodiments, CD47 variants of the present invention include CD47 variants having phosphorylated amino acid residues, e.g. phosphotyrosine, phosphoserine, or phosphothreonine.

In one embodiment, the high affinity CD47 reagent has a kinetic $K_D$ of at least about $1 \times 10^{-8}$ M for SIRPα. In another embodiment, the high affinity CD47 reagent has a kinetic $K_D$ of at least about $1 \times 10^{-8}$ M for SIRPα. In yet another embodiment, the high affinity CD47 reagent has a kinetic $K_D$ of at least about $1 \times 10^{-10}$ M for SIRPα. In various embodiments described herein, the high affinity CD47a reagent exhibits a kinetic $K_D$ to SIRPα that is at least about 5-fold greater than the kinetic $K_D$ of the native human CD47 polypeptide, exemplified in SEQ ID NO:1 and 2. In some embodiments, the high affinity CD47 reagent has a kinetic $K_D$ to SIRPα that is at least about 10-fold, 50-fold, 100-fold, 500-fold, 1000-fold greater than the kinetic $K_D$ of the native CD47 polypeptide.

Binding to SIRPα can be determined in any convenient manner. For example, binding can be determined by the ability of the CD47 reagent to bind to SIRPα coated on an assay plate; displayed on a microbial cell surface; in solution; etc. The binding activity of CD47 variants of the present invention to SIRPα can be assayed by immobilizing the ligand, e.g., the CD47 variant or the SIRPα, to a bead, substrate, cell, etc. Agents can be added in an appropriate buffer and the binding partners incubated for a period of time at a given temperature. After washes to remove unbound material, the bound protein can be released with, for example, SDS, buffers with a high pH, and the like and analyzed.

In some embodiments, a CD47 variant of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. In other embodiments, the second polypeptide is any suitable polypeptide that is substantially similar to Fc, e.g., providing increased size, multimerization domains, and/or additional binding or interaction with Ig molecules. These fusion proteins can facilitate purification, multimerization, and show an increased half-life in vivo. Fusion proteins having disulfide-linked multimeric structures can also be more efficient in binding and neutralizing other molecules than a monomeric CD47.

In some embodiments the high affinity CD47 reagent is provided as a multimeric protein, i.e. two, three, four or more high affinity CD47 reagents are covalently or non-covalently linked, e.g. as a fusion protein; disulfide bonded; through biotin binding to avidin, streptavidin, etc. Such multimeric high affinity CD47 binding proteins are useful as single agents to increase phagocytosis of cells expressing CD47 by binding SIRPα on the phagocytic cells; or in combination with other binding agents, e.g. cell-specific monoclonal antibodies.

In some such embodiments, the high affinity CD47 reagent is fused or otherwise joined to an immunoglobulin sequence to form a chimeric protein. The immunoglobulin sequence preferably, but not necessarily, is immunoglobulin constant domain(s). The immunoglobulin moiety in such chimeras may be obtained from any species, usually human, and includes IgG1, IgG2, IgG3 or IgG4 subtypes, IgA, IgE, IgD or IgM. The immunoglobulin moiety may comprise one or more domains, e.g. CH1, CH2, CH3, etc.

Chimeras constructed from a sequence linked to an appropriate immunoglobulin constant domain sequence are known in the art. In such fusions the encoded chimeric polypeptide may retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. The precise site at which the fusion is made is not critical; particular sites are well known and may be selected in order to optimize the biological activity, secretion or binding characteristics of the CD47 polypeptide-immunoglobulin chimeras. In some embodiments, the CD47 polypeptide-immunoglobulin chimeras are assembled as monomers, or hetero- or homo-multimers, and particularly as dimers or tetramers.

Although the presence of an immunoglobulin light chain is not required, an immunoglobulin light chain may be included, either covalently associated to a CD47 polypeptide-immunoglobulin heavy chain fusion polypeptide, or directly fused to the CD47 polypeptide. A single chain construct may be used to provide both heavy and light chain constant regions.

In other fusion protein constructs, the second polypeptide is a marker sequence, such as a peptide that facilitates purification of the fused polypeptide. For example, the marker amino acid sequence can be a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86: 821-824, 1989, for instance, hexa-histidine provides for convenient purification of the fusion protein. Another peptide tag useful for purification, the "HA" tag, corresponds to an epitope derived from the influenza hemagglutinin protein. Wilson et al., Cell 37: 767, 1984. The addition of peptide moieties to facilitate handling of polypeptides are familiar and routine techniques in the art.

In other embodiments the high affinity CD47 reagent is provided as a monomeric protein. Monomeric CD47 binding domains are useful, for example, as an adjuvant to increase the phagocytosis of cells expressing CD47, when combined with a cell-specific binding agent, e.g. an antibody, particularly a tumor cell specific antibody as defined herein. Monomeric CD47 reagents are also useful as adjuvants for increasing phagocytosis, as well as other immune functions, e.g. ADCC, uptake of antigens for antigen presentation, and the like by a number of immune cells, such as macrophages, dendritic cells, neutrophils, granulocytes and the like, which express SIRPα and respond to blockade with the CD47 reagents of the invention. Monomeric high affinity CD47 reagents are also useful as imaging agents, e.g. when conjugated to a detectable label.

In some other embodiments, high affinity CD47 reagents of the invention include reagents further modified to improve their resistance to proteolytic degradation or to optimize solubility properties or to render them more suitable as a therapeutic agent. For example, variants of the present invention further include analogs containing residues other than naturally occurring L-amino acids, e.g. D-amino acids or non-naturally occurring synthetic amino acids. D-amino acids may be substituted for some or all of the amino acid residues.

In some embodiments of the invention, the high affinity CD47 reagent is coupled or conjugated to one or more imaging moieties, i.e. a detectable label. As utilized herein, "imaging moiety", or detectable label, refers to a moiety that can be utilized to increase contrast between a tumor and the surrounding healthy tissue in a visualization technique, e.g., radiography, positron-emission tomography, magnetic resonance imaging, direct or indirect visual inspection. Thus, suitable imaging moieties include radiography moieties, e.g.

heavy metals and radiation emitting moieties, positron emitting moieties, magnetic resonance contrast moieties, and optically visible moieties (e.g., fluorescent or visible-spectrum dyes, visible particles, etc. It will be appreciated by one of ordinary skill that some overlap exists between what is a therapeutic moiety and what is an imaging moiety.

In certain embodiments, the high affinity CD47 reagent is coupled or conjugated to one or more therapeutic moieties, or cytotoxic moieties. As used herein, "cytotoxic moiety" refers to a moiety that inhibits cell growth or promotes cell death when proximate to or absorbed by the cell. Suitable cytotoxic moieties in this regard include radioactive isotopes (radionuclides), chemotoxic agents such as differentiation inducers and small chemotoxic drugs, toxin proteins, and derivatives thereof.

In general, therapeutic or imaging agents can be conjugated to the high affinity CD47 reagent moiety by any suitable technique, with appropriate consideration of the need for pharmacokinetic stability and reduced overall toxicity to the patient. A direct reaction between an agent and CD47 is possible when each possesses a functional group capable of reacting with the other. For example, a nucleophilic group, such as an amino or sulfhydryl group, may be capable of reacting with a carbonyl-containing group, such as an anhydride or an acid halide, or with an alkyl group containing a good leaving group (e.g., a halide). Alternatively, a suitable chemical linker group may be used. A linker group can function as a spacer in order to avoid interference with binding capabilities.

It will be evident to those skilled in the art that a variety of bifunctional or polyfunctional reagents, both homo- and hetero-functional (such as those described in the catalog of the Pierce Chemical Co., Rockford, Ill.), may be employed as a linker group. Coupling may be effected, for example, through amino groups, carboxyl groups, sulfhydryl groups or oxidized carbohydrate residues. There are numerous references describing such methodology. Alternatively the SIRPα is linked to the cytotoxic or imaging moiety by the use of a non-covalent binding pair, such as streptavidin/biotin, or avidin/biotin. In these embodiments, one member of the pair is covalently coupled to CD47 and the other member of the binding pair is covalently coupled to the cytotoxic or imaging moiety. It may be desirable to couple more than one cytotoxic and/or imaging moiety. By polyderivatizing the high affinity SIRPα reagent, several strategies may be simultaneously implemented, an antibody may be made useful as a contrasting agent for several visualization techniques, or a therapeutic antibody may be labeled for tracking by a visualization technique.

A carrier may bear the agents in a variety of ways, including covalent bonding either directly or via a linker group, and non-covalent associations. Suitable covalent-bond carriers include proteins such as albumins, peptides, and polysaccharides such as aminodextran, each of which have multiple sites for the attachment of moieties. A carrier may also bear an agent by non-covalent associations, such as non-covalent bonding or by encapsulation Carriers and linkers specific for radionuclide agents include radiohalogenated small molecules and chelating compounds. A radionuclide chelate may be formed from chelating compounds that include those containing nitrogen and sulfur atoms as the donor atoms for binding the metal, or metal oxide, radionuclide.

Radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the compositions and methods of the invention. Such moieties may be conjugated to the high affinity CD47 reagent antibody moiety through an acceptable chemical linker or chelation carrier. Positron emitting moieties for use in the present invention include $^{18}F$, which can be easily conjugated by a fluorination reaction with the high affinity CD47 reagent.

Magnetic resonance contrast moieties include chelates of chromium(III), manganese(II), iron(II), nickel(II), copper (II), praseodymium(III), neodymium(III), samarium(III) and ytterbium(III) ion. Because of their very strong magnetic moment, the gadolinium(III), terbium(III), dysprosium(III), holmium(III), erbium(III), and iron(III) ions are especially preferred.

Optically visible moieties for use as imaging moieties include fluorescent dyes, or visible-spectrum dyes, visible particles, and other visible labeling moieties. Fluorescent dyes such as fluorescein, coumarin, rhodamine, bodipy Texas red, and cyanine dyes, are useful when sufficient excitation energy can be provided to the site to be inspected visually. Endoscopic visualization procedures may be more compatible with the use of such labels. Acceptable dyes include FDA-approved food dyes and colors, which are non-toxic, although pharmaceutically acceptable dyes which have been approved for internal administration are preferred.

The effective amount of an imaging conjugate composition to be given to a particular patient will depend on a variety of factors, several of which will be different from patient to patient. A competent clinician will be able to determine an effective amount to facilitate the visualization of a SIRPα expressing cell, e.g., a phagocytic cell. Dosage will depend on the treatment of the tumor, route of administration, the nature of the therapeutics, sensitivity of the tumor to the therapeutics, etc. Utilizing ordinary skill, the competent clinician will be able to optimize the dosage of a particular therapeutic or imaging composition in the course of routine clinical trials.

A typical dose may be from 0.001 to 100 milligrams of conjugate per kilogram subject body weight. Relatively large doses, in the range of 0.1 to 10 mg per kilogram of patient body weight may be used for imaging conjugates with a relatively non-toxic imaging moiety. The amount utilized will depend on the sensitivity of the imaging method, and the relative toxicity of the imaging moiety.

CD47 variants of the present invention can be produced by any suitable means known or later discovered in the field, e.g., produced from eukaryotic or prokaryotic cells, synthesized in vitro, etc. Where the protein is produced by prokaryotic cells, it may be further processed by unfolding, e.g. heat denaturation, DTT reduction, etc. and may be further refolded, using methods known in the art.

The polypeptides may be prepared by cell-free translation systems, or synthetic in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized. One of skill in the art can readily utilize well-known codon usage tables and synthetic methods to provide a suitable coding sequence for any of the polypeptides of the invention. The nucleic acids may be isolated and obtained in substantial purity. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome. The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art.

According to the present invention, CD47 variants can be provided in pharmaceutical compositions suitable for therapeutic use, e.g. for human treatment. In some embodiments, pharmaceutical compositions of the present invention include one or more therapeutic entities of the present invention or pharmaceutically acceptable salts, esters or solvates thereof. In some other embodiments, pharmaceutical compositions of the present invention include one or more therapeutic entities of the present invention in combination with another therapeutic agent, e.g., another anti-tumor agent.

Therapeutic entities of the present invention are often administered as pharmaceutical compositions comprising an active therapeutic agent and a other pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions of the present invention can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

Polynucleotides encoding high affinity CD47 variants as described herein are also provided. It is noted that the generation of a polynucleotide encoding a given polypeptide is routine in the art (given the knowledge in the art of which codon(s) encodes each amino acid) and can be achieved in any convenient manner, including site directed mutagenesis of a parent polynucleotide sequence (e.g., one encoding a wild type CD47 polypeptide), synthetically, or a combination thereof. No limitation in this regard is intended.

The present invention also relates to nucleic acid constructs comprising a polynucleotide encoding a high affinity CD47 variant of the present invention operably linked to one or more control sequences that direct the expression of the coding sequence in a suitable host cell under conditions compatible with the control sequences.

The control sequence may be a promoter, which is a polynucleotide sequence (or combination of sequences) that is recognized by a host cell for expression of the polynucleotide. The promoter contains transcriptional control sequences that mediate the expression of the variant. The promoter may be any polynucleotide that shows transcriptional activity in a host cell of interest including mutant, truncated, and hybrid promoters, and may be obtained from genes encoding extracellular or intracellular polypeptides either homologous or heterologous to the host cell.

The control sequence may also be a transcription terminator, which is recognized by a host cell to terminate transcription. The terminator sequence is operably linked to the 3'-terminus of the polynucleotide encoding the variant. Any terminator that is functional in a host cell of interest may be used.

The present invention also relates to recombinant expression vectors comprising a polynucleotide encoding a high affinity CD47 variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the high affinity CD47 variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The present invention also relates to recombinant host cells, comprising a polynucleotide encoding a high affinity CD47 variant of the present invention operably linked to one or more control sequences that direct the production of the high affinity CD47 variant. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source. The host cell may be any cell useful in the recombinant production of a variant, e.g., a prokaryote or a eukaryote.

Methods of Use

Methods are provided for treating, reducing or preventing cancer, including without limitation lymphomas, leukemias, carcinomas, melanomas, glioblastomas, sarcomas, myelomas, etc. as primary or metastatic cancers, by inhibiting the interaction between SIRPα and CD47, thereby increasing in vivo phagocytosis of the tumor cells. Such methods include administering to a subject in need of treatment a therapeutically effective amount or an effective dose of a high affinity CD47 reagent of the invention, including without limitation combinations of the reagent with a chemotherapeutic drug, a tumor-specific antibody, or an ESA.

Effective doses of the therapeutic entity of the present invention, e.g. for the treatment of cancer, vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

In some embodiments, the therapeutic dosage may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still other embodiments, methods of the present invention include treating, reducing or preventing tumor growth, tumor metastasis or tumor invasion of cancers including lymphomas, leukemias, carcinomas, melanomas, glioblastomas, sarcomas, myelomas, etc. For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

The high affinity CD47 polypeptides of the invention may be used in vitro in binding assays in which they can be utilized in liquid phase or bound to a solid phase carrier. In addition, the polypeptides in these immunoassays can be detectably labeled in various ways. Examples of types of assays which can utilize high affinity CD47 polypeptides of the invention are flow cytometry, e.g. FACS, MACS, histochemistry, competitive and non-competitive immunoassays in either a direct or indirect format; and the like. Detection of SIRPα using the high affinity CD47 polypeptides can be done with assays which are run in either the forward, reverse, or simultaneous modes, including histochemical assays on physiological samples. Those of skill in the art will know, or can readily discern, other assay formats without undue experimentation.

The high affinity CD47 polypeptides can be bound to many different carriers and used to detect the presence of SIRPα expressing cells. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding proteins, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the polypeptides of the invention, or will be able to ascertain such, using routine experimentation. Furthermore, the binding of these labels to the polypeptides of the invention can be done using standard techniques common to those of ordinary skill in the art.

SIRPα may be detected by the high affinity CD47 polypeptides of the invention when present in biological fluids and tissues. Any sample containing a detectable amount of SIRPα can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis.

Another labeling technique which may result in greater sensitivity consists of coupling the polypeptides to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

The imaging conjugates of a high affinity CD47 reagent can be administered to the subject in a series of more than one administration. The imaging conjugate compositions may be administered at an appropriate time before the visualization technique. For example, administration within an hour before direct visual inspection may be appropriate, or administration within twelve hours before an MRI scan may be appropriate. Care should be taken, however, to not allow too much time to pass between administration and visualization, as the imaging compound may eventually be cleared from the patient's system.

Compositions for the treatment of cancer can be administered by parenteral, topical, intravenous, intratumoral, oral, subcutaneous, intraarterial, intracranial, intraperitoneal, intranasal or intramuscular means. A typical route of administration is intravenous or intratumoral, although other routes can be equally effective.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the high affinity CD47 reagents described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

Also within the scope of the invention are kits comprising the compositions (e.g., high affinity CD47 reagents and formulations thereof) of the invention and instructions for use. The kit can further contain a least one additional reagent, e.g. a chemotherapeutic drug, anti-tumor antibody, ESA, etc. Kits typically include a label indicating the intended use of the contents of the kit. The term label includes any writing, or recorded material supplied on or with the kit, or which otherwise accompanies the kit.

The invention now being fully described, it will be apparent to one of ordinary skill in the art that various changes and modifications can be made without departing from the spirit or scope of the invention.

EMBODIMENTS

The present disclosure includes the following non-limiting embodiments.

1. Aspects of the disclosure include a CD47 polypeptide variant, wherein the variant and comprises at least one amino acid modification relative to the wild-type CD47 sequence, and wherein the amino acid modification increases the affinity of the CD47 polypeptide binding to a SIRPα.

2. The variant of embodiment 1, wherein the variant lacks a transmembrane domain.

3. The variant of embodiment 1 or 2, wherein the variant has at least 100-fold increased affinity for a SIRPα.

4. The variant of any preceding embodiment, wherein the variant is a variant of human CD47.

5. The variant of any preceding embodiment, wherein the variant has at least 80% sequence identity to SEQ ID NO:4.

6. The variant of any preceding embodiment, wherein the variant comprises at least 1 amino acid added to the N-terminus of the mature protein.

7. The variant of any preceding embodiment, wherein the variant comprises at least 2 amino acids added to the N-terminus of the mature protein.

8. The variant of any preceding embodiment, wherein the variant comprises at least 3 amino acids added to the N-terminus of the mature protein.

9. The variant of embodiment 8, wherein the 3 amino acids added has the formula $X_{-3}X_{-2}X_{-1}$, where $X_{-3}$ is W; $X_{-2}$ is selected from Q, A and G; and $X_{-1}$ is selected from R, P, L, T, F, I, and M.

10. The variant of embodiment 9, wherein the three amino acids added are selected from: WQR, WAP, WQL, WQP, WQT, WQF, WQI, WGP, and WQM.

11. The variant of any preceding embodiment, wherein the protein comprises at least one amino acid substitution.

12. The variant of embodiment 11, wherein the at least one amino acid substitution is at an amino acid position selected from the group consisting of: Q1, L3, A53, and L54, wherein the amino acid positions are numbered according to SEQ ID NO:2.

13. The variant of embodiment 12, wherein the at least one amino acid substitution comprises one or more substitutions selected from the group consisting of: (1) Q1P and Q1L; (2) L3R, L3A, L3K, L3N, L3E, and L3V; (3) A53W, A53Y, A53D, A53Q, and A53V; and (4) L54A, L54T, L54K, L54M, L54E, L54W, L54S, L54I, and L54V.

14. The variant of embodiment 13, wherein the variant comprises modifications selected from items (1) to (4) at two, three, or all four of the amino aid positions.

15. The variant of any preceding embodiment, wherein the variant comprises the amino acid modifications in FIG. 4A.

16. The variant of any preceding embodiment, wherein the variant comprises an amino acid sequence selected from the group consisting of: SEQ ID NO: 5, SEQ ID NO:6, SEQ ID NO:7, and SEQ ID NO:8.

17. The variant of any preceding embodiment, wherein the variant is fused to an immunoglobulin Fc sequence.

18. The variant of any preceding embodiment, wherein the variant is provided in multimeric form.

19. The variant of any one of embodiments 1 to 17, wherein the variant is provided in monomeric form.

20. The variant of any preceding embodiment, wherein the variant further comprises a detectable label.

21. Aspects of the present disclosure include a therapeutic formulation comprising the CD47 polypeptide variant of any preceding embodiment.

22. Aspects of the present disclosure include a method of enhancing phagocytosis of a cell expressing CD47, the method comprising contacting the cell with an effective dose of a CD47 polypeptide variant according to any one of embodiments 1 to 20 or the therapeutic formulation of embodiment 21.

23. The method of embodiment 22, wherein the variant is administered in a combination with at least one additional factor.

24. The method of embodiment 23, wherein the additional factor is an antibody specific for a surface marker on the cell expressing CD47.

25. The method of embodiment 24, wherein the antibody is a tumor specific antibody.

26. The method of any one of embodiments 22 to 25, wherein the contacting is in vitro.

27. The method of any one of embodiments 22 to 25, wherein the contacting is in vivo.

28. The method of any one of embodiments 22 to 27, wherein the cell expressing CD47 is a cancer cell.

29. Aspects of the present disclosure include a method of imaging phagocytes, the method comprising contacting phagocytes with a polypeptide as set forth in embodiment 20.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

High-Affinity CD47 Lowers the Threshold for Macrophage Phagocytosis of Cancer Cells The ability of tumors to evade the immune system is an emerging hallmark of cancer, and new therapeutic strategies that direct immune responses against cancer cells show promise in experimental and clinical settings. Macrophages commonly infiltrate tumors, and recent studies have identified CD47 as an anti-phagocytic "don't eat me" signal that is highly expressed on many types of cancer to avoid macrophage-mediated destruction. Antibodies that block binding of CD47 to SIRPα, an inhibitory receptor on macrophages, greatly increase phagocytosis of cancer cells—identifying an exciting new axis to manipulate with anti-tumor immunotherapies. Directed evolution and protein engineering were used to modify the binding domain of SIRPα, whose wild-type affinity is too weak to be therapeutically useful, as a high-affinity competitive antagonist of CD47.

We created CD47 variants that bind to SIRPα alleles with an approximately 1,000-fold increase in affinity relative to wild-type CD47. While single domain high-affinity CD47 monomers are not sufficient to induce phagocytosis on their own, they greatly enhance the efficacy of established therapeutic monoclonal antibodies when given in combination therapies. Since CD47 is a pervasive mechanism that tumor cells use to evade the immune system, the molecules generated in this study benefit a large number of cancer patients, both as monotherapies and as adjuvants to other targeted biologics.

Figure 3A:
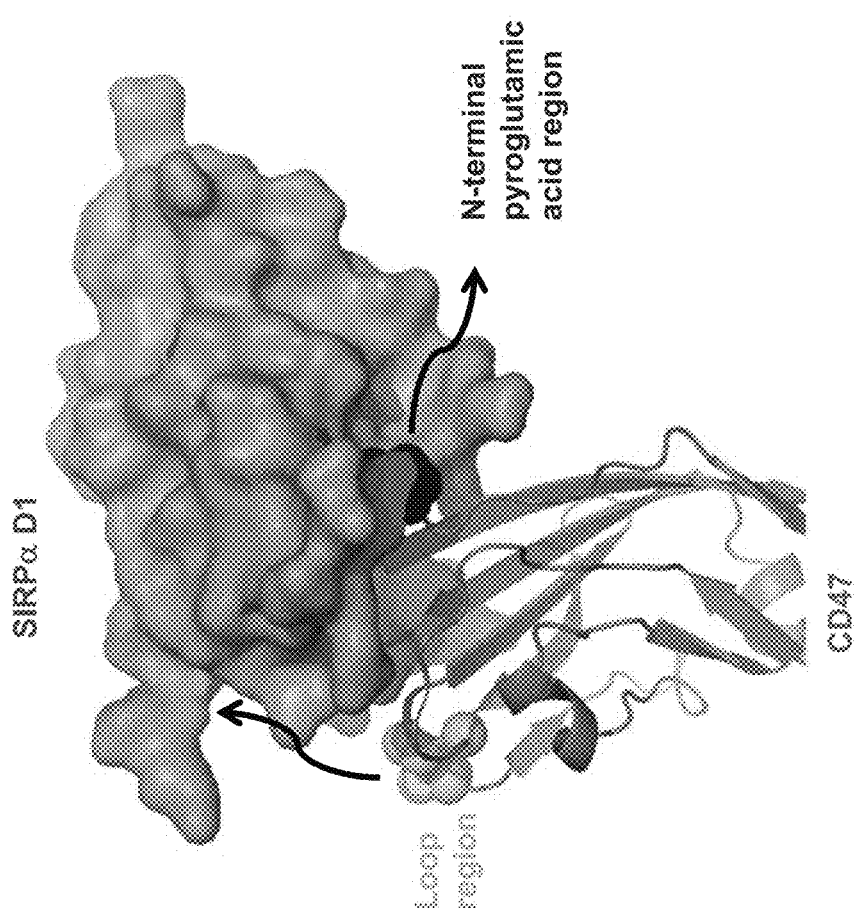
FIGS. 3A, 3B and 3C. CD47 variant library design and selection summary. Directed evolution of high-affinity CD47 variants.
Figure 3B:
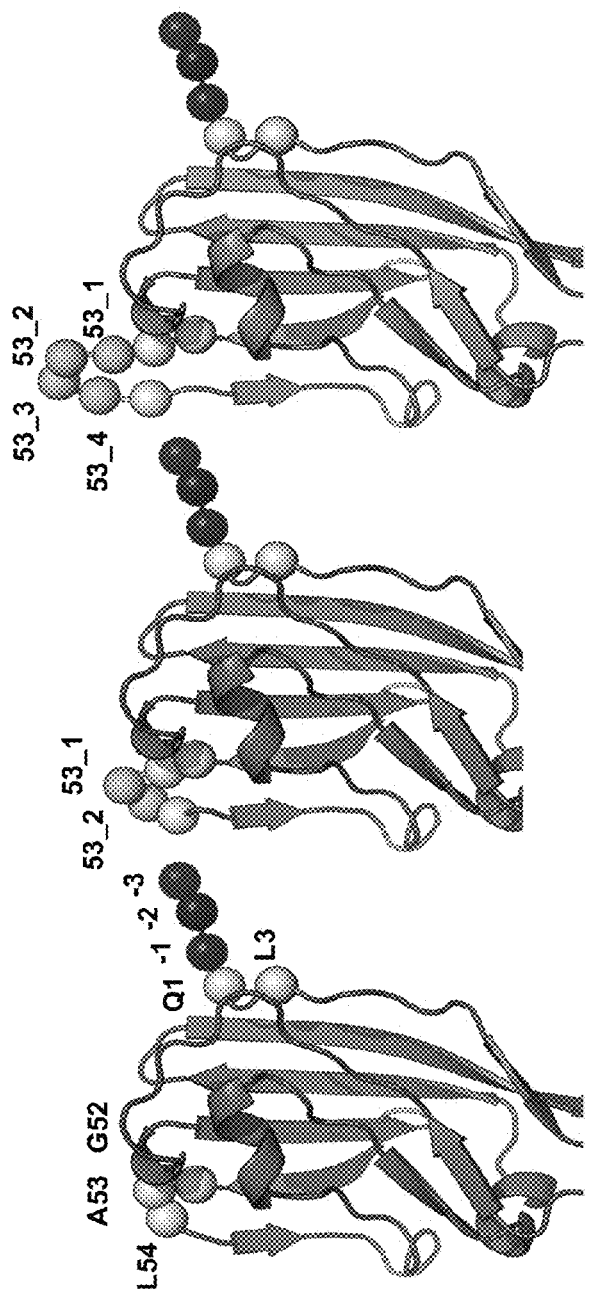
Figure 3C:
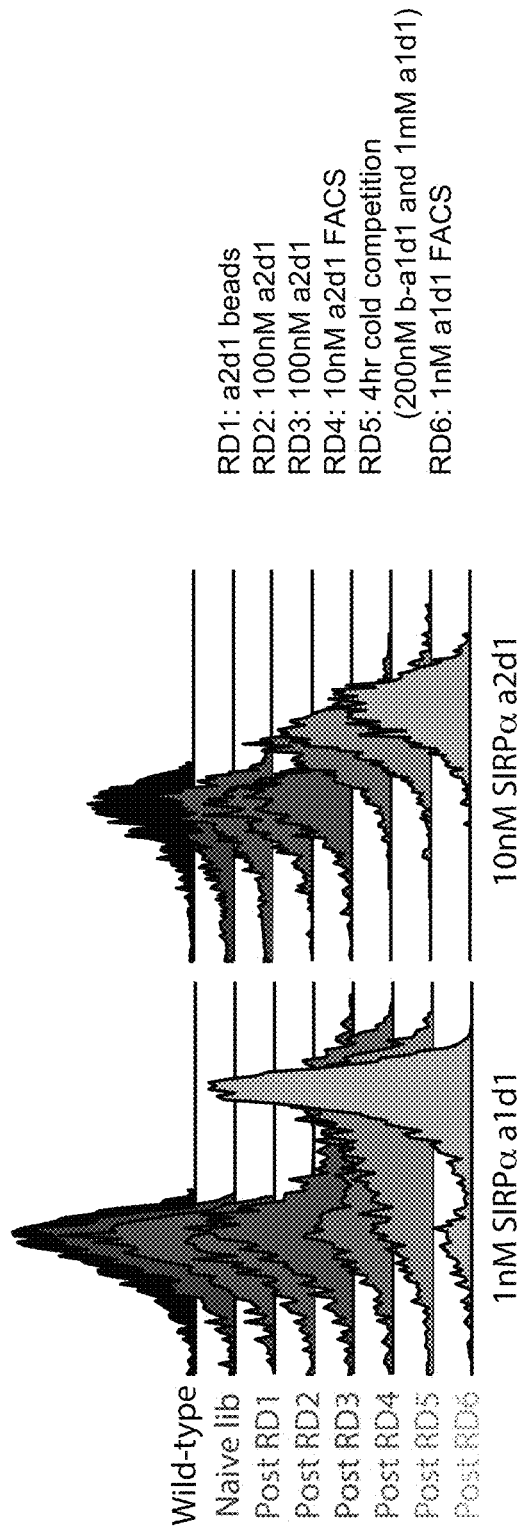

To generate an ideal CD47 antagonist, protein engineering was used to improve the affinity of soluble CD47 for SIRPα (FIG. 3). FIG. 3A shows a schematic of the interaction between CD47 (bottom) and SIRPα (top; green), which is based on the previously described crystal structure. The strategy taken for generating variants that increase CD47 affinity for SIRPα includes by N-terminal (dark blue; right arrow in FIG. 3A) and/or loop extensions (light blue; left arrow in FIG. 3A). Extending one of both of these regions of CD47 is predicted to promote higher affinity interactions with SIRPα. We created three mutant libraries of the IgSF domain of CD47 conjugated to Aga2p for yeast surface-display (FIG. 3B) and combined them for screening for have high-affinity for SIRPα binders. FIG. 3B shows representations of these three libraries (left, middle, and right), with −1, −2, −3 denoting the 3 additional residues at the N-terminal region (any amino acid); 53_x denoting the additional random amino acid residues at the Loop region between A53 and L54 [0 (left), 2 (middle), or 4 (right) total insertions], and Q1, L3, G52, A53 and L54 sites indicated (each were randomized to any amino acid). FIG. 3C shows histogram overlays assessing SIRPα a1d1 (Left) and a2d1 (Right) staining of the library at each round of selection (denoted RD1 to RD6; see Methods section below for a description of these steps).

Figure 4B:
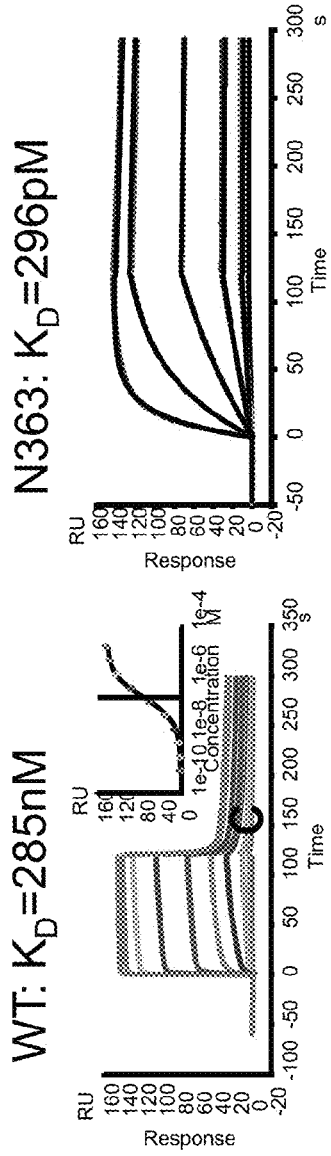
Figure 4C:
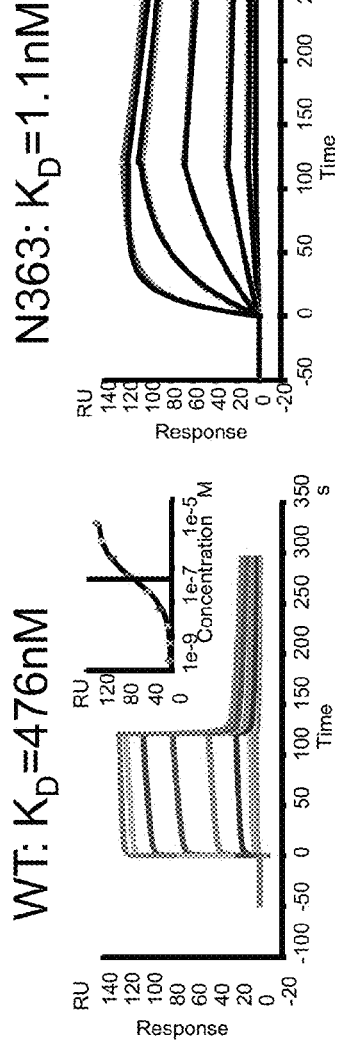

FIG. 4A provides representative sequences of high affinity CD47 variants obtained in the selection process described above. In this table, the positions in CD47 are shown on top (which correspond to the positions indicated in FIG. 3B), the clone name is on the left with the wildtype sequence shown first (WT), and the amino acid at each position in the clone is listed if it is different than the WT sequence. Red text indicates a consensus amino acid. In FIG. 4B shows surface plasmon resonance (SPR) assays of WT CD47 (left) and a representative high affinity CD47 variant N363 (right) binding to human SIRPα allele 1 domain 1 (a1d1). As shown in FIG. 4B, WT CD47 bound SIRPα (a1d1) with a dissociation constant ($K_D$) of 285 nM while the high affinity CD47 variant N363 bound SIRPα (a1d1) with a $K_D$ of 296 pM. Thus, this high affinity CD47 variant has an approximate 1000-fold increase in its $K_D$ with SIRPα (a1d1) as compared to WT CD47. As shown in FIG. 4C, WT CD47 bound SIRPα (a2d1) with a dissociation constant ($K_D$) of 476 nM while the high affinity CD47 variant N363 bound SIRPα (a2d1) with a $K_D$ of 1.1 nM. Thus, this high affinity CD47 variant has an approximate 400-fold increase in its $K_D$ with SIRPα (a2d1) as compared to WT CD47. FIG. 4D shows the full amino acid sequences for the N363 C15G (SEQ ID NO:5), N3612 C15G (SEQ ID NO:6), N3612 C15 (SEQ ID NO:7) and N3612 F14C (SEQ ID NO:8) high affinity CD47 variants.

FIGS. 5A-5B. High affinity CD47 monomer is an adjuvant to monoclonal antibodies to increase phagocytosis of cancer cells. Ex vivo functional characterization of high affinity CD47 analogs. A) Primary human macrophage phagocytosis of GFP+Raji lymphoma (Left), GFP+SKBR3 breast cancer (Middle) and GFP+DLD-1 colon cancer (Right) cells treated with PBS (Blue, WT CD47 monomer (Red), high affinity N3612 clone (Orange; SEQ ID NO:6) or Super-SIRP CV1 (Purple) with or without respective tumor-specific monoclonal antibodies. Proteins were used at 1 uM, and the antibodies were used at 10 ug/ml. B) Dose-response of macrophage phagocytosis of GFP+SKBR3 breast cancer (Left) and GFP+DLD-1 colon cancer (Right) cells treated with titrating amounts of tumor-specific monoclonal antibodies in the presence of 1 uM protein treatments.

Figure 6A:
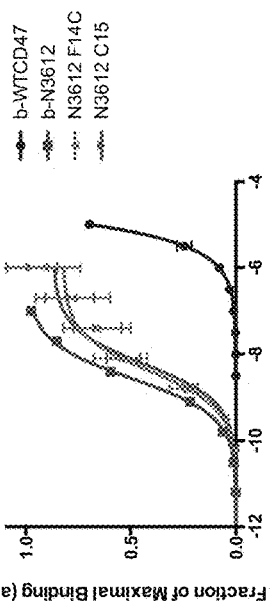
FIGS. 6A, 6B, 6C and 6D. Reformatting high affinity CD47 variant into a diagnostic agent.
Figure 6B:
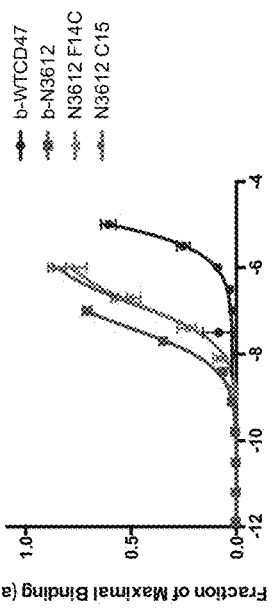
Figure 6C:
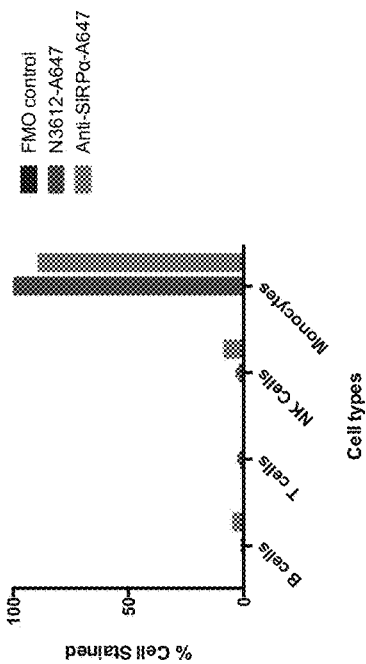
Figure 6D:
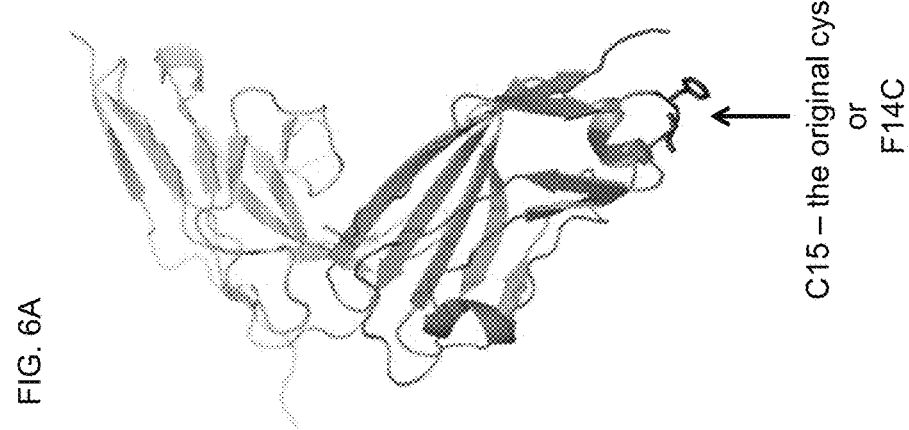

High affinity CD47 variants were modified to produce diagnostic agents. FIG. 5A shows schematics of the Cysteine mutation installed for maleimide linking chemistry. In the original high affinity CD47 variants isolated, the cysteine at position 15 (C15) had been changed to a G (C15G variants). To enable coupling of high affinity CD47 variants to a fluorescent moiety, position 15 was reverted to a Cysteine (C15) or the Phenylalanine (F) at position 14 was changed to a Cysteine (F14C). Binding of such reagents to SIRPα was tested. FIG. 6B: titration of biotinylated WT CD47 (Blue), biotinylated unmodified high affinity CD47 variant N3612 (Red), N3612 F140 coupled to Alexa Fluor 647 (Green), and N3612 C15 coupled to Alexa Fluor 647 (Purple) on-SIRPα a1d1 expressing yeast. FIG. 6C: titration of biotinylated WT CD47 (Blue), biotinylated unmodified high affinity CD47 variant N3612 (Red), N3612 F140 coupled to Alexa Fluor 647 (Green), and N3612 C15 coupled to Alexa Fluor 647 (Purple) on-SIRPα a2d1 expressing yeast. FIG. 6D: Staining of human peripheral blood using FMO control (Blue), high affinity CD47 variant N3612-Alexa 647 (Red), and a commercially available anti-SIRP antibody-Alexa 647 (Green). As shown in these figures, the high affinity CD47 reagents can detect SIRPα expression on cells, both engineered and non-engineered, much better than the wildtype molecule. Indeed, as show in FIG. 6D, these reagents can perform as well as anti-SIRPα antibody in such assays.

The development of the high-affinity SIRPα variants represents a multidisciplinary, rational drug design effort, proceeding from molecular engineering at the protein level, to in vitro validation using purified immune effector cells, and finally to therapeutic evaluation in animal models. While previous studies have demonstrated the value of targeting the CD47-SIRPα interaction as an immune intervention for cancer, here we have further manipulated this system to generate highly efficacious and potent CD47 antagonists that exhibit optimal properties as therapeutics.

The high-affinity CD47 reagents provided herein constitute a novel class of anti-tumor biologics that are amenable to further engineering. Modifications can be designed to alter efficacy, specificity, tissue penetrance, clearance, and toxicity. CD47 is commonly used by tumor cells to evade the immune system, thus high-affinity CD47 variants could be valuable therapeutics for a variety of human cancers. Moreover, high-affinity CD47 monomers can be used as universal adjuvants to conventional monoclonal antibody therapies. Overall, this study deepens our knowledge of macrophage responses to malignant cells and supports use of the high-affinity CD47 reagents as immune-based therapies for cancer.

Methods

Protein Expression and Purification.

Human SIRPα allele 1 domain 1 (a1d1), allele 2 domain 1 (a2d1) and CV1 were expressed as previously described (Weiskopf et al. (2013) Engineered SIRPα variants as immunotherapeutic adjuvants to anticancer antibodies. Science 341, 88-91). Briefly, SIRPα variants were cloned into a modified pMal-p2X expression vector (New England Biolabs) containing a 3C protease cleavage site (LEVLFQ/GP) after the maltose-binding protein (MBP) tag and a C-terminal 8× histidine tag, and expressed in the periplasm of BL-21(DE3) E. coli. Cells were induced with 1 mM IPTG and incubated with shaking at room temperature (rt) overnight. MBP-fusion protein was purified by nickel-nitrilotriacetic acid (Ni-NTA) resin (Qiagen) then digested with 3C protease (produced in house) at 4° C. overnight to remove the MBP tag. SIRPα proteins were further purified by Ni-NTA affinity chromatography, followed by size exclusion chromatography using a Superdex-75 column (GE Healthcare).

Human CD47 IgSF domain (residues 19-135 in FIG. 2) and high-affinity CD47 variants (sometimes called "Velcro" variants), both with a C15G mutation (Hatherley et al. (2008) Paired receptor specificity explained by structures of signal regulatory proteins alone and complexed with CD47. Mol Cell 31, 266-277) and C-terminal 8× histidine tag, were cloned into pAcGP67a using Gibson assembly (24) to remove N-terminal scar from restriction enzyme digestion of the plasmid, ensuring a free N-terminus. The plasmids were transfected into Trichoplusia ni (High Five) cells (Invitrogen) using the Baculogold baculovirus expression system (BD Biosciences) for secretion and purified by Ni-NTA and size exclusion chromatography with a Superdex-75 column.

Biotinylated CD47 and SIRPα variants were expressed with a carboxy-terminal biotin acceptor peptide tag (GLN-DIFEAQKIEWHE; SEQ ID NO:9) and purified as described above. The purified proteins were biotinylated in vitro with BirA ligase and then re-purified from the reaction mixture by size exclusion chromatography.

For profiling human peripheral blood, CV1 A17C and N3612 F14C were expressed and purified as described above to allow site-specific conjugation via maleimide linking chemistry. The proteins were conjugated to Alexa Fluorophore 647 maleimide (Life Technologies) according to manufacturer's protocol and re-purified from the reaction mixture by size exclusion chromatography.

For in vitro phagocytosis assays, endotoxin was removed using Triton X-114 as previously described (Weiskopf et al. (2013) Engineered SIRPalpha variants as immunotherapeutic adjuvants to anticancer antibodies. Science 341, 88-91), and endotoxin removal was confirmed using the ToxinSensor Chromogenic LAL Endotoxin Assay Kit (Genscript).

Yeast Display and Construction of the CD47 Extension Library

The human CD47 IgSF domain, with a C15G mutation (Hatherley et al. (2014) Polymorphisms in the human inhibitory signal-regulatory protein alpha do not affect binding to its ligand CD47. The Journal of biological chemistry 289, 10024-10028), was displayed on the surface of S. cerevisiae strain EBY100 as an N-terminal fusion to Aga2 using the pYAL vector (Birnbaum et al. (2014) Deconstructing the peptide-MHC specificity of T cell recognition. Cell 157, 1073-1087), leaving a free N-terminus.

To construct the CD47 Extension library, the mutagenized CD47 DNA constructs from N3L0, N3L2 and N3L4 molecule designs were mixed and combined with linearized pYAL vector and EBY100 yeast.

N3L0 molecule design extends the N-terminus by 3 additional residues and randomizes Q1, L3, G52, A53 and L54.

N3L2 molecule design, extends the N-terminus by 3 additional residues, extends the FG loop region by 2 additional residues, and randomizes Q1, L3, G52, A53 and L54.

N3L4 molecule design, extends the N-terminus by 3 additional residues, extends the FG loop region by 4 additional residues, and randomizes Q1, L3, G52, A53 and L54.

The NNK codon was used at all of the positions randomized and/or extended. Electroporation, rescue and expansion of the yeast library were performed as described previously (Boder, E. T., and Wittrup, K. D. (1997) Yeast surface display for screening combinatorial polypeptide libraries. Nat Biotechnol 15, 553-557). Final library contained approximately 3×10$^8$ yeast transformants.

Selection of the CD47 Extension Library

The selections of the yeast library were performed as described previously with some modifications (Weiskopf et al. (2013) Engineered SIRPalpha variants as immunotherapeutic adjuvants to anticancer antibodies. Science 341, 88-91). Briefly, the initial selections (rounds 1-3) were conducted using magnetic activated cell sorting (MACS). For round 1, $1.0 \times 10^9$ cells were selected with paramagnetic streptavidin microbeads (Miltenyi) that were pre-coated with 400 nM biotinylated SIRPα a2d1. For rounds 2 and 3, $1.0 \times 10^8$ yeast were stained and selected with 100 nM monomeric biotinylated SIRPα a2d1. To normalize apparent affinity by protein expression on the cell surface, library selection was performed using two-color fluorescence activated cell sorting (FACS) in the subsequent rounds. After incubation with target protein during each subsequent round, yeast library was washed twice and co-labeled with streptavidin-Alexa Fluor 647 (SIRPα binding) and anti-cMyc-Alexa Fluor 488 (CD47 variant expression) for 10 minutes at 4° C. Alexa647$^+$Alexa488$^+$ yeast were purified using a FACS Jazz cell sorter (BD Biosciences). For round 4, the yeast library was stained using 10 nM monomeric biotinylated SIRPα a2d1 for 1 hour at 4° C. For round 5, the yeast library was incubated with 200 nM biotinylated SIRPα a1d1 for 1 hour at rt, washed twice with PBE (PBS, pH 7.4+0.5% (w/v) BSA+2 mM EDTA, pH 8.0) and competed with 1 μM unbiotinylated SIRPα a1d1 for 4 hours at rt. For round 6, the yeast library was stained with 1 nM SIRPα a1d1 for 1 hour at 4° C.

After the sixth round of selection, 100 μL of the yeast library, which was expanded in SD-CAA medium over night, was collected to extract library DNA using the Zymoprep™ Yeast Plasmid Miniprep II kit (Zymo Research), according to manufacturer's instructions. The extracted DNA was transformed into DH5a *E. coli* and plated to sequence individual colonies.

Surface Plasmon Resonance

The binding affinity and kinetics were measured using a Biacore T100 (GE Healthcare). Protein concentrations were quantified by 280 nM absorbance using a Nanodrop2000 spectrometer (Thermo Scientific). Biotinylated SIRPα a1d1 and a2d1 was immobilized on a Biacore SA sensor chip (GE Healthcare) in different flow channels with a Rmax ~150 RU (response unit) and ~130 RU, respectively. An unrelated biotinylated protein was captured in another flow channel with a similar RU value to control for nonspecific binding. Experiments were carried out at 25° C., and measurements were made with serial dilutions of CD47 variants in HBS-P+ buffer (GE Healthcare) supplemented with 0.1% (w/v) BSA. All data were analyzed with the Biacore T100 evaluation software version 2.0 with a 1:1 Langmuir binding model.

Cell-Based SIRPα Blocking Assay

Biotinylated wild-type CD47 was incubated with Alexa Fluor 647-conjugated streptavidin for 15 minutes at rt to form CD47 tetramers. Labeled human (for human cells) or mouse (for mouse cells) CD47 tetramer at 100 nM were combined with serial dilutions of unlabeled CD47 variants and simultaneously added to stain undifferentiated THP-1, human macrophages or NSG (NOD scid gamma) splenocytes. Cells were incubated for 1 hour at 4° C., then washed with PBE to remove unbound proteins. Samples were analyzed on an Accuri C6 flow cytometer (BD Biosciences). Data represent the mean fluorescence intensity normalized to maximal binding for each class of reagents, and points were fit to sigmoidal dose-response curves using Prism 5 (Graphpad).

In Vitro Macrophage Phagocytosis

Macrophage derivation and phagocytosis experiments were conducted as previously described (Weiskopf et al. (2013) Engineered SIRPalpha variants as immunotherapeutic adjuvants to anticancer antibodies. Science 341, 88-91).

Briefly, human macrophages were isolated from leukocyte reduction system (LRS) chambers (Stanford Blood Center) using anti-CD14 whole blood magnetic beads (Miltenyi) and purified with autoMACS Pro Separator (Miltenyi). The cells were cultured in IMDM+GlutaMax (Life Technologies) supplemented with 10% human Ab serum (Invitrogen) for 7-10 days. Assays were performed by incubation of macrophages with GFP$^+$ tumor cells at 1:2 ratio in serum-free medium at 37° C. for 2 hours. Phagocytosis was analyzed using an LSRFortessa cell analyzer with high throughput sampler (BD Biosciences) and evaluated as the percentage of GFP$^+$ macrophages using FlowJo v9.4.10 (Tree Star, Inc.). The data were normalized to the maximal response by each independent donor against each cell line and were fit to sigmoidal dose-response curves using Prism5 (Graphpad).

Human Immune Cell Profiling

The CD47 and SIRPα expression profile on various blood cell populations was determined by multi-color flow cytometry. A human buffy coat was obtained from Stanford Blood Center and treated with ACK lysing buffer to remove red blood cells (RBCs) (Life Technologies). Cells ($1 \times 10^6$/well, 100 μL) were stained with markers for B-cells (CD19$^+$CD20$^+$), CD4-T-cells (CD3$^+$CD4$^+$), CD8-T-cells (CD3$^+$CD8$^+$), NK-cells (CD3$^-$CD14$^-$CD19$^-$CD16$^+$CD56$^+$), monocytes (FSC$^{hi}$CD14$^+$), neutrophils (SSC$^{hi}$CCR3$^-$CD16$^+$), eosinophils (SSC$^{hi}$CCR3$^+$CD16$^-$), and basophils (CD3$^-$CD14$^-$CD19$^-$CD56$^-$SSC$^{lo}$CD123$^{hi}$CCR3$^+$) in PBS containing 2% human serum and 0.1 mg/mL mouse serum IgG as described previously (Mori et al. (2009) Identification of the human eosinophil lineage-committed progenitor: revision of phenotypic definition of the human common myeloid progenitor. The Journal of experimental medicine 206, 183-193). RBCs (CD235a$^+$) were stained directly from freshly isolated heparinized human whole blood (Stanford Blood Center). Dead cells were excluded by propidium iodide (PI) (Life Technologies) staining, and single cells were selected based on SSC and FSC properties. The fluorescence minus one (FMO) method was used to determine the threshold of negative versus positive staining. The samples were co-stained with anti-CD47 (high-affinity SIRPα CV1) or anti-SIRPα (high-affinity CD47 N3612, 15-414, REA144, SE5A5) agents. CV1-Alexa Fluor 647 and N3612-Alexa Fluor 647 were used at 250 nM. Anti-SIRPα clone 15-414 (eBioscience), clone REA144 (Miltenyi), and clone SE5A5 (BioLegend) were used at 1:50 dilution. All analyses were performed on LSRFortessa cell analyzer with high throughput sampler (BD Biosciences), and data was analyzed with FlowJo software (Tree Star, Inc.).

---

SEQUENCES

SEQ ID NO: 1
Full length Human CD47 sequence
Genbank: gi|728797214|emb|CEJ95640.1|
MWPLVAALLLGSACCGSAQLLFNKTKSVEFTFCNDTVVIPCFVTNMEAQN
TTEVYVKWKFKGRDIYTFDGALNKSTVPTDFSSAKIEVSQLLKGDASLKM
DKSDAVSHTGNYTCEVTELTREGETIIELKYRVVSWFSPNENILIVIFPI
FAILLFWGQFGIKTLKYRSGGMDEKTIALLVAGLVITVIVIVGAILFVPG
EYSLKNATGLGLIVTSTGILILLHYYVFSTAIGLTSFVIAILVIQVIAYI
LAVVGLSLCIAACIPMHGPLLISGLSILALAQLLGLVYMKFVE SEQ ID NO: 2
Mature, membrane bound CD47.
QLLFNKTKSVEFTFCNDTVVIPCFVTNMEAQNTTEVYVKWKFKGRDIYTF
DGALNKSTVPTDFSSAKIEVSQLLKGDASLKMDKSDAVSHTGNYTCEVTE
LTREGETIIELKYRVVSWFSPNENILIVIFPIFAILLFWGQFGIKTLKYR
SGGMDEKTIALLVAGLVITVIVIVGAILFVPGEYSLKNATGLGLIVTSTG
ILILLHYYVFSTAIGLTSFVIAILVIQVIAYILAVVGLSLCIAACIPMHG
PLLISGLSILALAQLLGLVYMKFVE

SEQUENCES

SEQ ID NO: 3
Extracellular domain
QLLFNKTKSVEFTFCNDTVVIPCFVTNMEAQNTTEVYVKWKFKGRDIYTF
DGALNKSTVPTDFSSAKIEVSQLLKGDASLKMDKSDAVSHTGNYTCEVTE
LTREGETIIELKYRVVSWFSPNENI SEQ ID NO: 4
IgSF domain
QLLFNKTKSVEFTFCNDTVVIPCFVTNMEAQNTTEVYVKWKFKGRDIYTF
DGALNKSTVPTDFSSAKIEVSQLLKGDASLKMDKSDAVSHTGNYTCEVTE
LTREGETIIELKYRVVS SEQ ID NO: 5
N363 C15G full amino acid sequence
WQLPLLFNKTKSVEFTFGNDTVVIPCFVTNMEAQNTTEVYVKWKFKGRDI
YTFDGDKNKSTVPTDFSSAKIEVSQLLKGDASLKMDKSDAVSHTGNYTCE
VTELTREGETIIELKYRVVS SEQ ID NO: 6
N3612 C15G full amino acid sequence
WQPPLLFNKTKSVEFTFGNDTVVIPCFVTNMEAQNTTEVYVKWKFKGRDI
YTFDGQANKSTVPTDFSSAKIEVSQLLKGDASLKMDKSDAVSHTGNYTCE
VTELTREGETIIELKYRVVS SEQ ID NO: 7
N3612 C15 full amino acid sequence
WQPPLLFNKTKSVEFTFCNDTVVIPCFVTNMEAQNTTEVYVKWKFKGRDI
YTFDGQANKSTVPTDFSSAKIEVSQLLKGDASLKMDKSDAVSHTGNYTCE
VTELTREGETIIELKYRVVS SEQ ID NO: 8
N3612 F14C full amino acid sequences
WQPPLLFNKTKSVEFTCGNDTVVIPCFVTNMEAQNTTEVYVKWKFKGRDI
YTFDGQANKSTVPTDFSSAKIEVSQLLKGDASLKMDKSDAVSHTGNYTCE
VTELTREGETIIELKYRVVS SEQ ID NO: 9. Biotin acceptor tag:
GLNDIFEAQKIEWHE

What is claimed is:

1. A CD47 polypeptide variant, wherein the variant comprises at least one amino acid modification relative to the wild-type CD47 sequence, wherein the amino acid modification increases the affinity of the CD47 polypeptide binding to a SIRPα, the modification comprising at least 3 amino acids added to the N-terminus of the mature protein wherein the 3 amino acids added has the formula $X_{-3}X_{-2}X_{-1}$, where $X_{-3}$ is W; $X_{-2}$ is selected from Q, A and G; and $X_{-1}$ is selected from R, P, L, T, F, I, and M.

2. The variant of claim 1, wherein the three amino acids added are selected from: WQR, WAP, WQL, WQP, WQT, WQF, WQI, WGP, and WQM.

3. The variant of claim 1, further comprising an amino acid substitution at an amino acid position selected from the group consisting of: Q1, L3, A53, and L54, wherein the amino acid positions are numbered according to SEQ ID NO:2.

4. The variant of claim 3, wherein the at least one amino acid substitution comprises one or more substitutions selected from the group consisting of: (1) Q1P and Q1L; (2) L3R, L3A, L3K, L3N, L3E, and L3V; (3) A53W, A53Y, A53D, A53Q, and A53V; and (4) L54A, L54T, L54K, L54M, L54E, L54W, L54S, L54I, and L54V.

5. The variant of claim 4, wherein the variant comprises a plurality of modifications selected from (1) Q1P and Q1L; (2) L3R, L3A, L3K, L3N, L3E, and L3V; (3) A53W, A53Y, A53D, A53Q, and A53V; and (4) L54A, L54T, L54K, L54M, L54E, L54W, L54S, L54I, and L54V.

6. The variant of claim 1, wherein the variant comprises the amino acid modifications selected from:
   addition of WQR added to the N-terminus of the mature protein and substitutions Q1P, L3R, A53W, L54A;
   addition of WAP added to the N-terminus of the mature protein and substitutions Q1P, L3R, A53Y, L54T;
   addition of WQL added to the N-terminus of the mature protein and substitutions Q1P, A53D, L54K;
   addition of WQP added to the N-terminus of the mature protein and substitutions Q1L, L3A, L54M;
   addition of WAP added to the N-terminus of the mature protein and substitutions Q1L, L3R;
   addition of WQT added to the N-terminus of the mature protein and substitutions Q1P, L3K;
   addition of WQF added to the N-terminus of the mature protein and substitutions Q1P, L3R, L54E;
   addition of WQI added to the N-terminus of the mature protein and substitutions Q1P, L3N, L54W;
   addition of WQP added to the N-terminus of the mature protein and substitutions Q1L, L54S;
   addition of WQP added to the N-terminus of the mature protein and substitutions Q1P, A53Q, L54A;

addition of WQP added to the N-terminus of the mature protein and substitutions Q1L, L3K, L54A;

addition of WQR added to the N-terminus of the mature protein and substitutions Q1P, L3R;

addition of WQL added to the N-terminus of the mature protein and substitutions Q1P, L54I;

addition of WQI added to the N-terminus of the mature protein and substitutions Q1P, L3E;

addition of WGP added to the N-terminus of the mature protein and substitutions Q1L, L3R;

addition of WQM added to the N-terminus of the mature protein and substitutions Q1P, L3V, A53V, L54T;

addition of WQI added to the N-terminus of the mature protein and substitutions Q1P, L3R, A53Q, L54V.

7. The variant of claim 1, wherein the variant comprises an amino acid sequence selected from the group consisting of: SEQ ID NO: 5, SEQ ID NO:6, SEQ ID NO:7, and SEQ ID NO:8.

8. The variant of claim 1, wherein the variant is fused to an immunoglobulin Fc sequence.

9. A therapeutic formulation comprising the CD47 polypeptide variant of claim 1.

10. A method of enhancing phagocytosis of a cell expressing CD47, the method comprising contacting the cell with an effective dose of a CD47 polypeptide variant according to claim 1.

11. The method of claim 10, wherein the variant is administered in a combination with at least one additional factor.

12. The method of claim 11, wherein the additional factor is a tumor specific antibody specific for a surface marker on the cell exp